(12) United States Patent
Wakana

(10) Patent No.: US 12,232,839 B2
(45) Date of Patent: Feb. 25, 2025

(54) SURGICAL TOOL, SURGERY SUPPORT SYSTEM, AND SURGICAL OPERATING UNIT

(71) Applicant: SONY GROUP CORPORATION, Tokyo (JP)

(72) Inventor: Kazuhito Wakana, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 416 days.

(21) Appl. No.: 17/753,530

(22) PCT Filed: Aug. 31, 2020

(86) PCT No.: PCT/JP2020/032851
§ 371 (c)(1),
(2) Date: Mar. 7, 2022

(87) PCT Pub. No.: WO2021/049345
PCT Pub. Date: Mar. 18, 2021

(65) Prior Publication Data
US 2022/0338946 A1 Oct. 27, 2022

(30) Foreign Application Priority Data
Sep. 13, 2019 (JP) .................................. 2019-166764

(51) Int. Cl.
*A61B 34/00* (2016.01)
(52) U.S. Cl.
CPC .................................. *A61B 34/71* (2016.02)

(58) Field of Classification Search
CPC . A61B 34/71; A61B 17/29; A61B 2034/2061; A61B 2034/305; A61B 2034/301; A61B 2034/715; A61B 34/35
See application file for complete search history.

(56) References Cited

U.S. PATENT DOCUMENTS

2010/0274078 A1* 10/2010 Kim ..................... A61B 34/30
600/102
2010/0274265 A1  10/2010 Wingardner et al.
(Continued)

FOREIGN PATENT DOCUMENTS

| CA | 2665627 A1 | 4/2008 |
|----|------------|--------|
| CN | 101522121 A | 9/2009 |

(Continued)

OTHER PUBLICATIONS

International Search Report and Written Opinion of PCT Application No. PCT/JP2020/032851, issued on Oct. 27, 2020, 10 pages of ISRWO.

*Primary Examiner* — Shaun L David
*Assistant Examiner* — Rachael L Geiger
(74) *Attorney, Agent, or Firm* — CHIP LAW GROUP

(57) ABSTRACT

Provided is a surgical tool that includes a shaft, a pitch unit that is connected to an end of the shaft and is able to turn about a first axis, a roll unit that is supported and is rotatable about a second axis with respect to the pitch unit, and a grip unit that is supported and is linearly movable in the second axis direction with respect to the roll unit. The surgical tool further includes a pair of jaws that are attached to the lower end of the roll unit in the second axis direction, and open and close in conjunction with linear motion of the grip unit in the second axis direction.

12 Claims, 29 Drawing Sheets

(56) References Cited

U.S. PATENT DOCUMENTS

| | | |
|---|---|---|
| 2015/0025571 A1 | 1/2015 | Suzuki et al. |
| 2016/0174967 A1* | 6/2016 | Taylor ................ A61B 17/0625 |
| | | 606/144 |
| 2017/0149323 A1 | 5/2017 | Gombert et al. |

FOREIGN PATENT DOCUMENTS

| | | |
|---|---|---|
| CN | 106471721 A | 3/2017 |
| DE | 102014009892 A1 | 1/2016 |
| EP | 2837341 A1 | 2/2015 |
| JP | 2010-505524 A | 2/2010 |
| JP | 2013-215502 A | 10/2013 |
| JP | 2017-527245 A | 9/2017 |
| JP | 2018-534100 A | 11/2018 |
| JP | 2019-501699 A | 1/2019 |
| KR | 10-2017-0028925 A | 3/2017 |
| WO | 2008/045367 A2 | 4/2008 |
| WO | 2013/154157 A1 | 10/2013 |
| WO | 2016/000823 A1 | 1/2016 |
| WO | 2018/003925 A1 | 1/2018 |
| WO | 2018/163680 A1 | 9/2018 |
| WO | 2019/096939 A1 | 5/2019 |

\* cited by examiner $\theta_{pitch} : 0^0$
$\theta_{roll} : 0^0$
$\theta_{grip} : 0^0$ $\theta_{pitch} : 0^0$
$\theta_{roll} : 0^0$
$\theta_{grip} : 10^0$ $\theta_{pitch} : 0°$
$\theta_{roll} : 0°$
$\theta_{grip} : 20°$ $\theta_{pitch} : 0°$
$\theta_{roll} : 150°$
$\theta_{grip} : 0°$ $\theta_{pitch} : 0^0$
$\theta_{roll} : 75^0$
$\theta_{grip} : 0^0$ $\theta_{pitch} : 0^0$
$\theta_{roll} : 0^0$
$\theta_{grip} : 0^0$ $\theta_{pitch} : 0°$
$\theta_{roll} : -75°$
$\theta_{grip} : 0°$ $\theta_{pitch} : 0°$
$\theta_{roll} : -140°$
$\theta_{grip} : 0°$ $\theta_{pitch} : 80^0$
$\theta_{roll} : 0^0$
$\theta_{grip} : 0^0$ $\theta_{pitch} : 40^0$
$\theta_{roll} : 0^0$
$\theta_{grip} : 0^0$ $\theta_{pitch} : 0°$
$\theta_{roll} : 0°$
$\theta_{grip} : 0°$ $\theta_{pitch} : -40°$
$\theta_{roll} : 0°$
$\theta_{grip} : 0°$ $\theta_{pitch} : -80°$
$\theta_{roll} : 0°$
$\theta_{grip} : 0°$ $\theta_{pitch} : 40°$
$\theta_{roll} : 0°$
$\theta_{grip} : 0°$ θ pitch : 40°
θ roll : 0°
θ grip : 20°

θ pitch : 40°
θ roll : 45°
θ grip : 20°

SURGICAL TOOL, SURGERY SUPPORT SYSTEM, AND SURGICAL OPERATING UNIT

CROSS REFERENCE TO RELATED APPLICATIONS

This application is a U.S. National Phase of International Patent Application No. PCT/JP2020/032851 filed on Aug. 31, 2020, which claims priority benefit of Japanese Patent Application No. JP 2019-166764 filed in the Japan Patent Office on Sep. 13, 2019. Each of the above-referenced applications is hereby incorporated herein by reference in its entirety.

TECHNICAL FIELD

The technology disclosed in this specification (hereinafter referred to as "the present disclosure") relates to a surgical tool to be used in a surgical robot, for example, a surgery support system, and a surgical operating unit.

BACKGROUND ART

Advances in the robotics technologies in recent years are remarkable, and robots are now widely used in work sites in various industrial fields. For example, in the field medicine, a master-slave surgical robot is becoming widespread. This kind of surgical robot is designed so that an operator such as a surgeon operates, from the master side, one or a plurality of surgical tools included in a slave device. Also, as a known method for controlling a master-slave system, there is a bilateral method by which a slave device is operated from a master device, and at the same time, the state of the slave device is fed back to the master device (see Patent Document 1, for example).

An end effector having an opening and closing mechanism such as forceps is provided at the end of a surgical tool mounted in a slave device. Further, on the assumption that a surgical tool is to be used in an operation in a body cavity, on a body surface, or the like, the end of a surgical tool is strongly desired to have multiple degrees of freedom, have a small diameter, be small in size, and be light in weight. Specifically, the end of a surgical tool is desired to have a total of three degrees of freedom, which are two degrees of freedom of rotation and a degree of freedom of opening and closing. Further, for miniaturization of surgical tools, a drive method using a cable is often adopted in handling the end of a surgical tool (see Patent Documents 2 to 4, for example).

CITATION LIST

Patent Documents

Patent Document 1: Japanese Patent Application Laid-Open No. 2019-34002
Patent Document 2: Japanese Patent Application Laid-Open No. 09-542671
Patent Document 3: JP 2018-534100 W
Patent Document 4: JP 2019-501699 W
Patent Document 5: WO 2018/163680

SUMMARY OF THE INVENTION

Problems to be Solved by the Invention

An object of the technology according to the present disclosure is to provide a surgical tool that has an open-close end effector such as forceps, is designed to be small in size and light in weight, and is used in a surgical robot, and to provide a surgery support system and a surgical operating unit.

Solutions to Problems

A first aspect of the technology according to the present disclosure is
a surgical tool that includes:
a shaft;
a pitch unit that is connected to an end of the shaft and is able to turn about a first axis;
a roll unit that is supported and is rotatable about a second axis with respect to the pitch unit; and
a grip unit that is supported and is linearly movable in the second axis direction with respect to the roll unit.

The surgical tool according to the first aspect further includes a pair of jaws that are attached to the lower end of the roll unit in the second axis direction, and open and close in conjunction with linear motion of the grip unit in the second axis direction.

The grip unit is linearly moved in the second axis direction by the tractive force generated in the set of first forward and backward cables when a first motor rotates a first drive capstan, and the pair of jaws then open and close in conjunction with the linear motion. Meanwhile, the roll unit is made to turn about the second axis by the tractive force generated in the set of second forward and backward cables when a second motor rotates a second drive capstan.

Further, when a third motor rotates a third drive capstan in the positive direction or the reverse direction, one of the set of first forward and backward cables and the set of second forward and backward cables is pulled in the longitudinal axis direction of the shaft, and thus, the pitch unit turns about the first axis.

Further, a second aspect of the technology according to the present disclosure is a surgery support system that includes a surgical tool, and an arm to which the surgical tool is attached,
the surgical tool including:
a shaft;
a pitch unit that is connected to an end of the shaft and is able to turn about a first axis;
a roll unit that is supported and is rotatable about a second axis with respect to the pitch unit; and
a grip unit that is supported and is linearly movable in the second axis direction with respect to the roll unit.

Furthermore, a third aspect of the technology according to the present disclosure is
a surgical operating unit that includes a surgical tool, and a handle unit to which the surgical tool is attached,
the surgical tool including:
a shaft;
a pitch unit that is connected to an end of the shaft and is able to turn about a first axis;
a roll unit that is supported and is rotatable about a second axis with respect to the pitch unit; and
a grip unit that is supported and is linearly movable in the second axis direction with respect to the roll unit.

Effects of the Invention

By the technology according to the present disclosure, it is possible to provide a surgical tool that has an open-close end effector such as forceps, includes a smaller number of components, has a smaller diameter, and is used in a surgical robot, and to provide a surgery support system and a surgical operating unit.

Note that the advantageous effects described in this specification are merely examples, and the advantageous effects to be brought about by the technology according to the present disclosure are not limited to them. Furthermore, in some cases, the technology according to the present disclosure may exhibit additional advantageous effects, in addition to the above advantageous effects.

Other objects, features, and advantages of the technology according to the present disclosure will be made apparent by the embodiments described below and the detailed descriptions with reference to the accompanying drawings.

MODE FOR CARRYING OUT THE INVENTION

Figure 1:
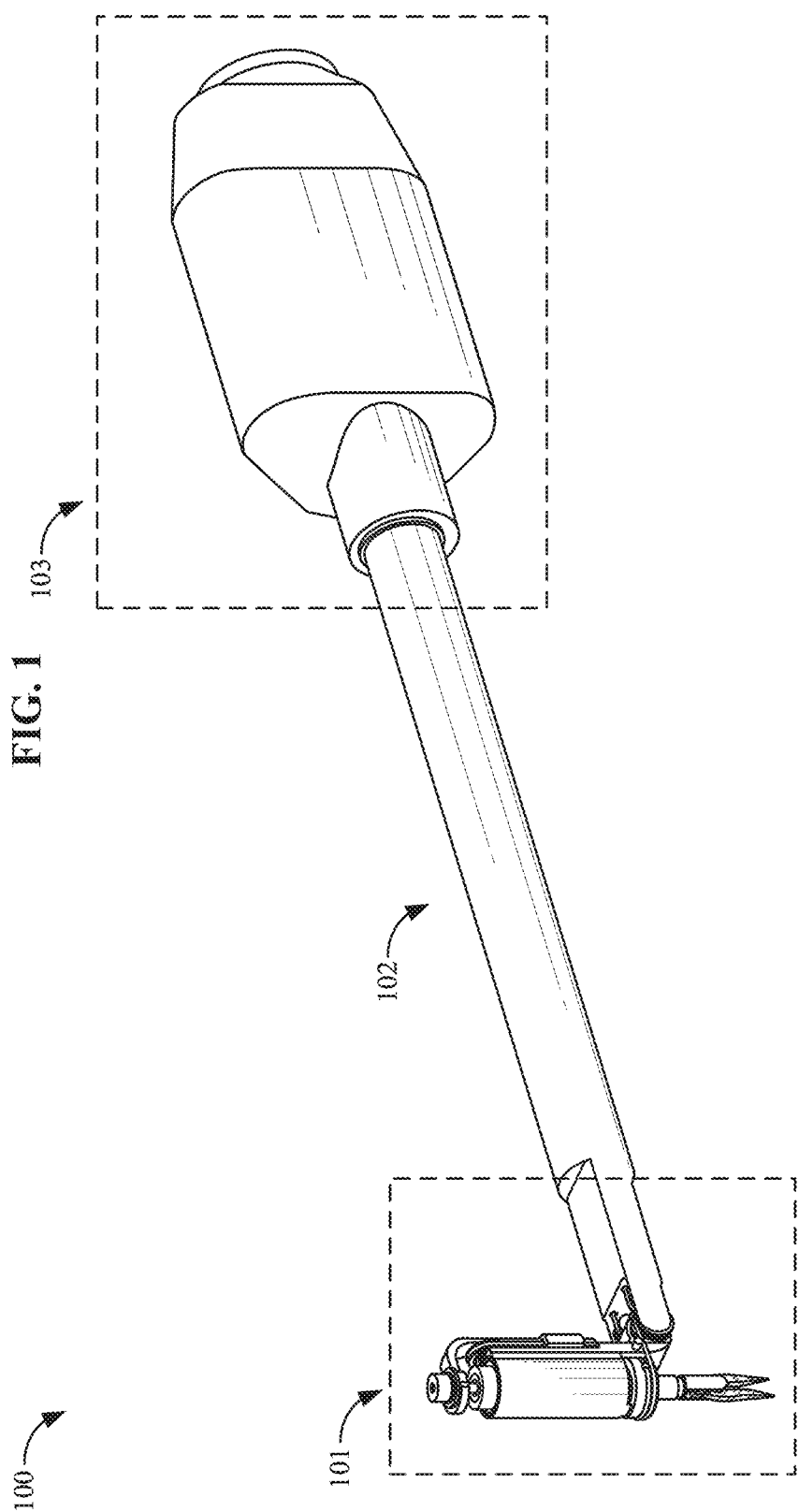
FIG. 1 is a diagram showing an example external configuration of a surgical tool unit 100.

In the description below, the technology according to the present disclosure will be explained in the following order, with reference to the drawings.

A. Problems with a Surgical Tool Unit
B. Example Configuration of a Surgical Tool Unit
C. Operations of a Surgical Tool Unit
D. Modifications of the Roll Unit
E. Modifications of the Surgical Tool Unit
F. Example Applications of the Surgical Tool Unit
G. Effects A. Problems with a Surgical Tool Unit A surgical tool to be used in a surgical robot preferably has a total of three degrees of freedom, which are two degrees of freedom of rotation and a degree of freedom of opening and closing at the end. For example, a surgical tool of a known type includes an open-close end effector formed with a pair of jaws, a wrist that supports the end effector, and a shaft that has a longitudinal axis and connects the wrist to its end. This kind of surgical tool has a degree-of-freedom configuration including: a first axis for turning the wrist about the yaw axis, for example, with respect to the end of the shaft; a second axis for turning the orientation of the end effector about the pitch axis, for example, with respect to the wrist; and a third axis (an open-close shaft) for opening and closing the jaws (see Patent Documents 2 to 4, for example).

In the case of such a degree-of-freedom configuration, the first axis and the second axis are both limited to movement within approximately ±90 degrees, due to restrictions on the range of movement of each link.

In the case of a surgical tool that is normally inserted into a body cavity through a trocar as in laparoscopic surgery, the diameter of the surgical tool needs to be made smaller at its end. Therefore, as described above, the surgical tool preferably has a configuration that has a first axis for turning the wrist about the yaw axis with respect to the end of the shaft, for example, and a second axis for turning the orientation of the end effector about the pitch axis with respect to the wrist, for example.

On the other hand, in the case of a surgical tool to be used in surgery on the body surface or in the vicinity of the body surface, the restrictions on reduction of the diameter at the end are relaxed, but a wider range of movement is required.

Therefore, this specification will suggest below a surgical tool unit that has a total of three degrees of freedom, which are two degrees of freedom of rotation and a degree of freedom of opening and closing at the end, and achieves a wider range of movement. A surgical tool unit according to the present disclosure is supposed to be used in surgery on the body surface or in the vicinity of the body surface, for example, but an objective thereof is to achieve a wider range of movement.

Specifically, a surgical tool unit according to the present disclosure includes a shaft with a longitudinal axis, a pitch unit, a roll unit, and a grip unit. The shaft supports the pitch unit at its end so that the pitch unit can turn about a first axis parallel to the pitch axis. Meanwhile, the pitch unit supports the roll unit rotatably about a second axis parallel to the roll axis. Also, the roll unit may support the grip unit formed with a pair of jaws that can open and close. Accordingly, the surgical tool unit according to the present disclosure has three degrees of freedom: a rotational degree of freedom of the pitch unit to turn about the first axis with respect to the end of the shaft; a rotational degree of freedom of the roll unit to turn about the second axis while being supported by the pitch unit; and a degree of freedom of opening and closing the pair of jaws.

As will be described later, in the surgical tool unit according to the present disclosure, the pitch unit has a range of movement of ±80 degrees about the first axis, and the roll unit has a range of movement of −140 to 150 degrees about the second axis. For example, in a case where the surgical tool unit is used in surgery on the body surface or near the body surface, it is safe to say that these ranges of movement are wide enough. Note that the maximum open-close angle of the pair of jaws is 20 degrees, for example.

In the embodiment described below, tractive force by cables is used to drive the pitch unit, the roll unit, and the grip unit (or the jaws). That is, the power of each actuator disposed on the root side (the proximal end side) of the shaft is transmitted to the pitch unit, the roll unit, and the grip unit on the end side (the distal end side) through cables.

Further, in a power transmission mechanism using cables, a plurality of pulleys may be used, such as capstans for applying power to the cables or converting the forces from the cables into axial forces, and idler pulleys to be used for adjusting the layout of the cables in the shaft and applying constant tension to the cables.

B. Example Configuration of a Surgical Tool Unit

Figure 2:
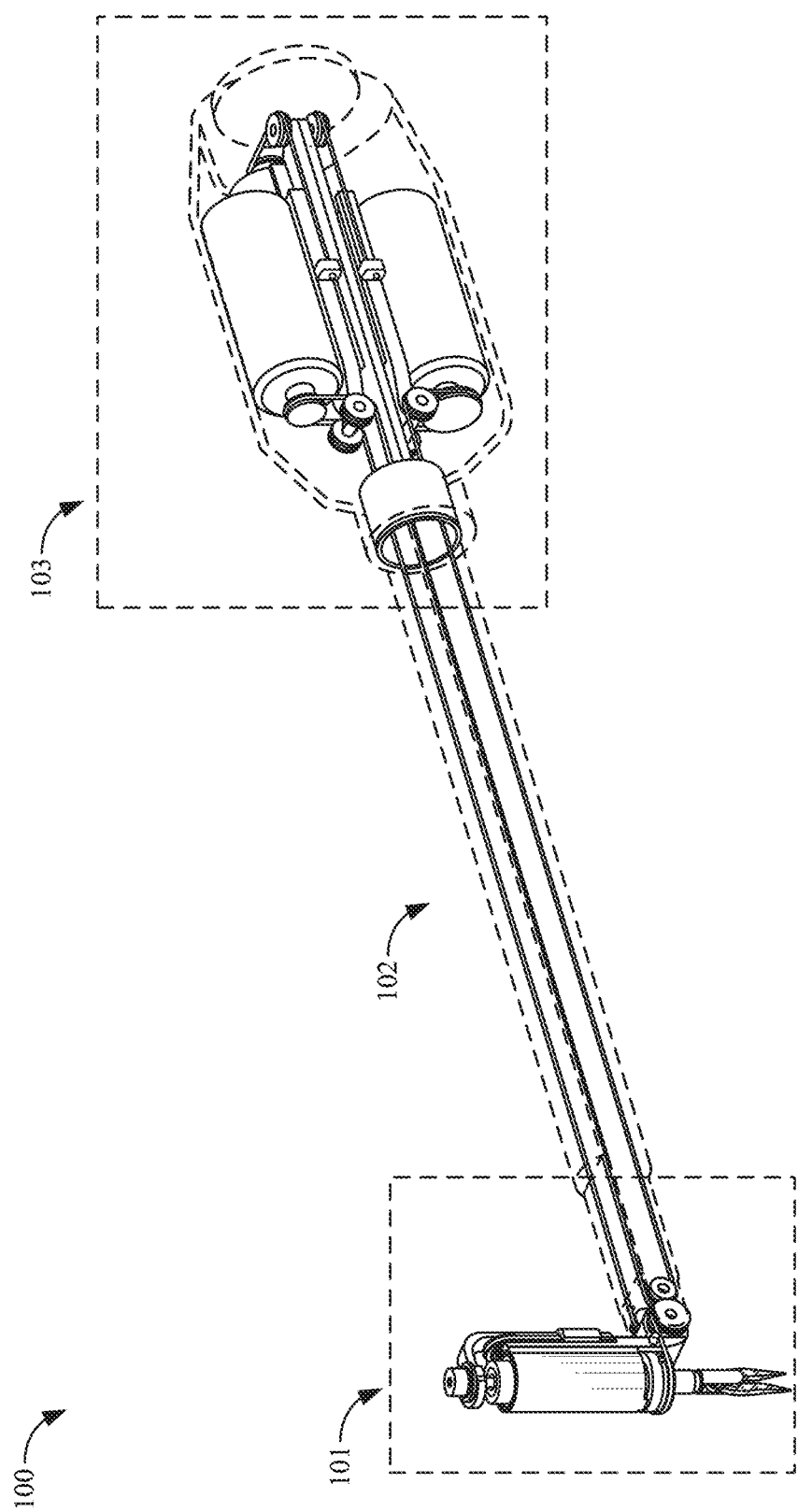
FIG. 2 is a diagram showing an example external configuration of the surgical tool unit 100.
Figure 3:
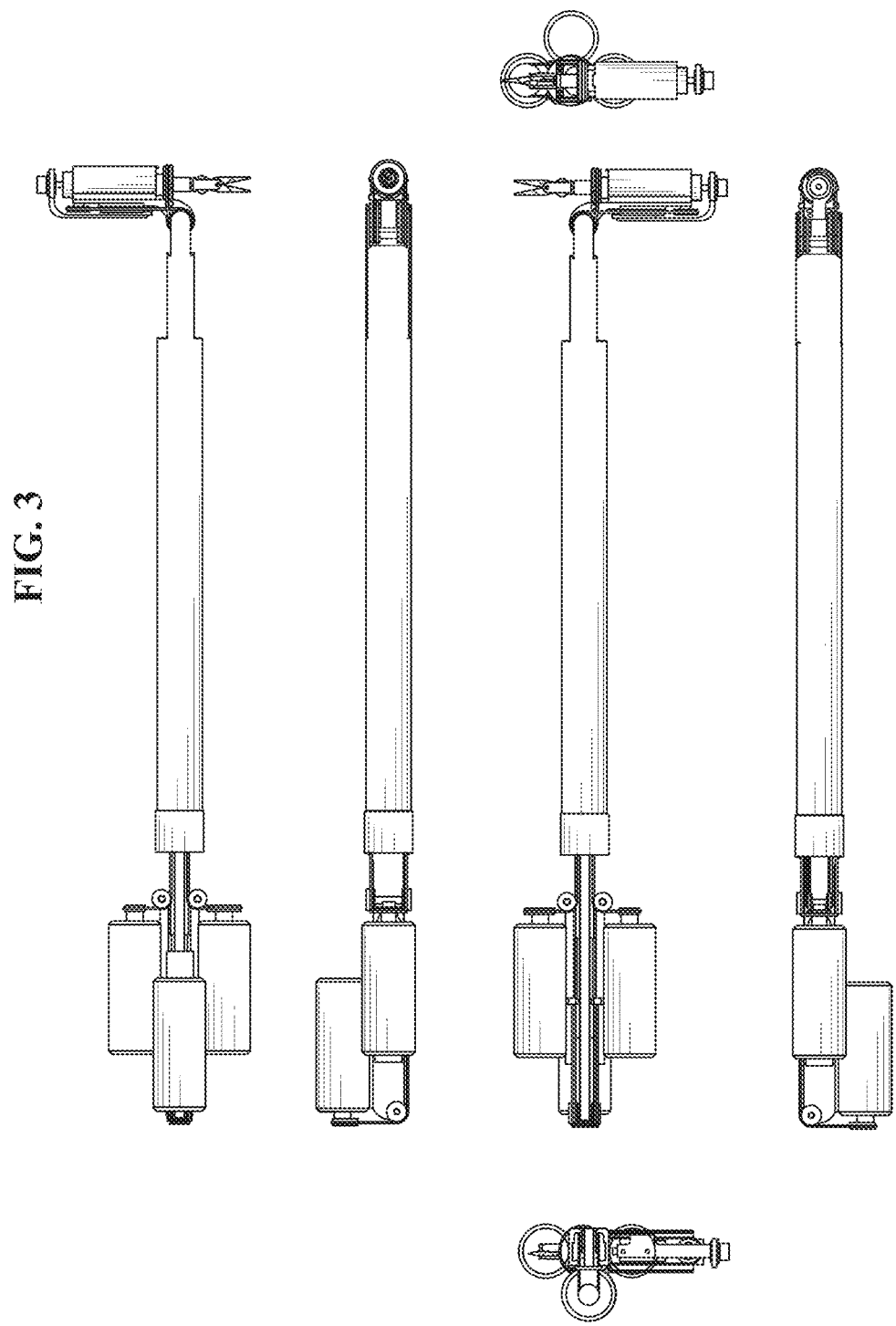
FIG. 3 is a six-sided view of the surgical tool unit 100.

FIGS. 1 and 2 show an example external configuration of a surgical tool unit according to the present disclosure. Further, FIG. 3 shows a six-sided view of the surgical tool unit. A surgical tool unit 100 shown in the drawing includes a hollow shaft 102 having a longitudinal axis, a surgical tool unit end portion 101 at one end of the shaft 102, and a surgical tool unit drive unit 103 at the other end of the shaft 102. FIG. 1 shows a perspective view of the surgical tool unit 100. FIG. 2 shows the shaft 102 and the surgical tool unit drive unit 103 in a transparent manner to make the inside thereof visible.

The surgical tool unit end portion 101 includes a pitch unit rotatable about a first axis parallel to the pitch axis with respect to the shaft 102, a roll unit supported by the pitch unit rotatably about a second axis parallel to the roll axis, and a grip unit supported by the roll unit. The grip unit includes a pair of jaws that can be opened and closed. However, the second axis is located at a position offset from the first axis.

Each movable portion of the surgical tool unit end portion 101 is driven by the tractive force of a cable. Further, actuators for pulling the respective cables are provided in the surgical tool unit drive unit 103. In this embodiment, electromagnetic rotary motors are used as the actuators. As shown in FIG. 2, a plurality of cables for driving the pitch unit, the roll unit, and the grip unit of the surgical tool unit end portion 101 is inserted through the shaft 102. Further, three motors for pulling the respective cables for driving the pitch unit, the roll unit, and the grip unit are provided in the surgical tool unit drive unit 101.

Figure 4:
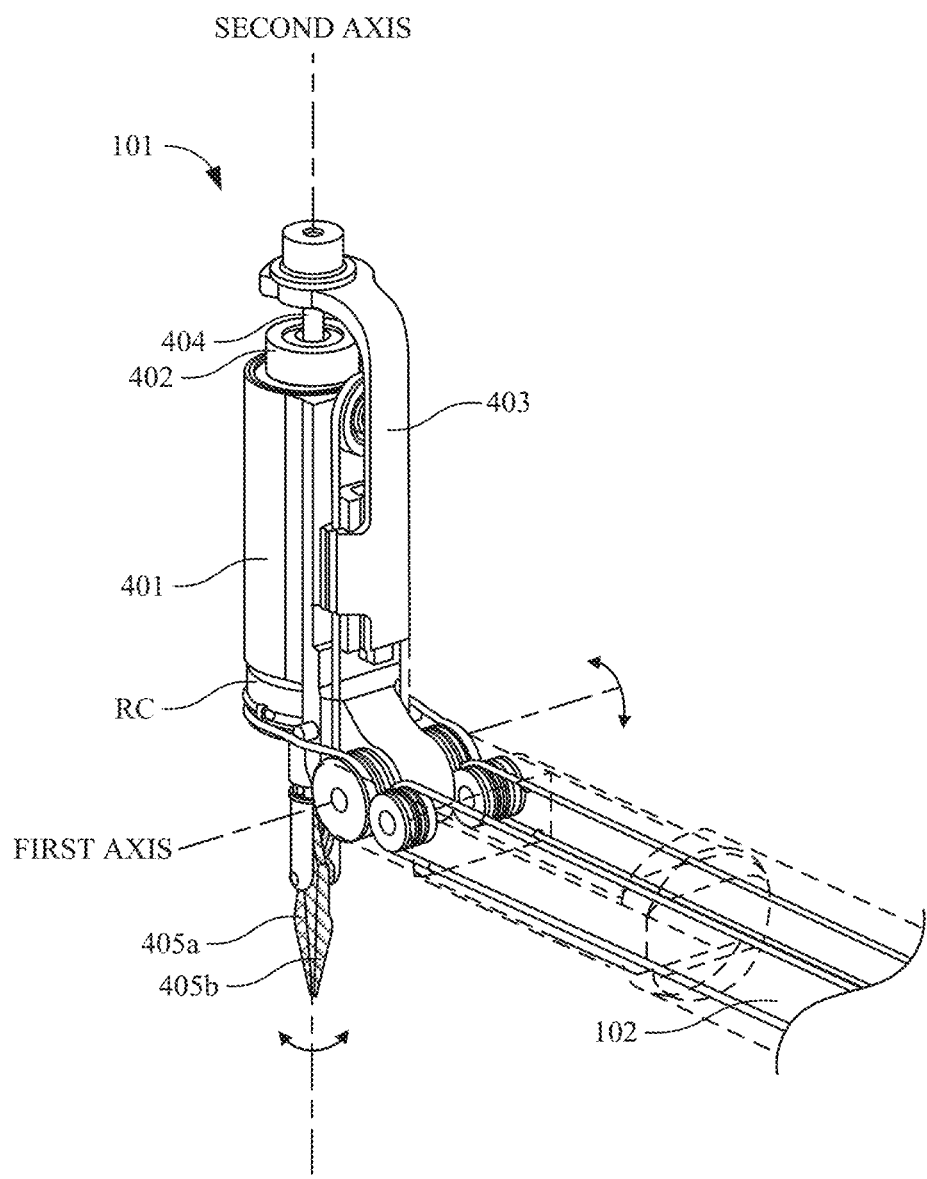
FIG. 4 is an enlarged view of a surgical tool unit end portion 101.
Figure 5:
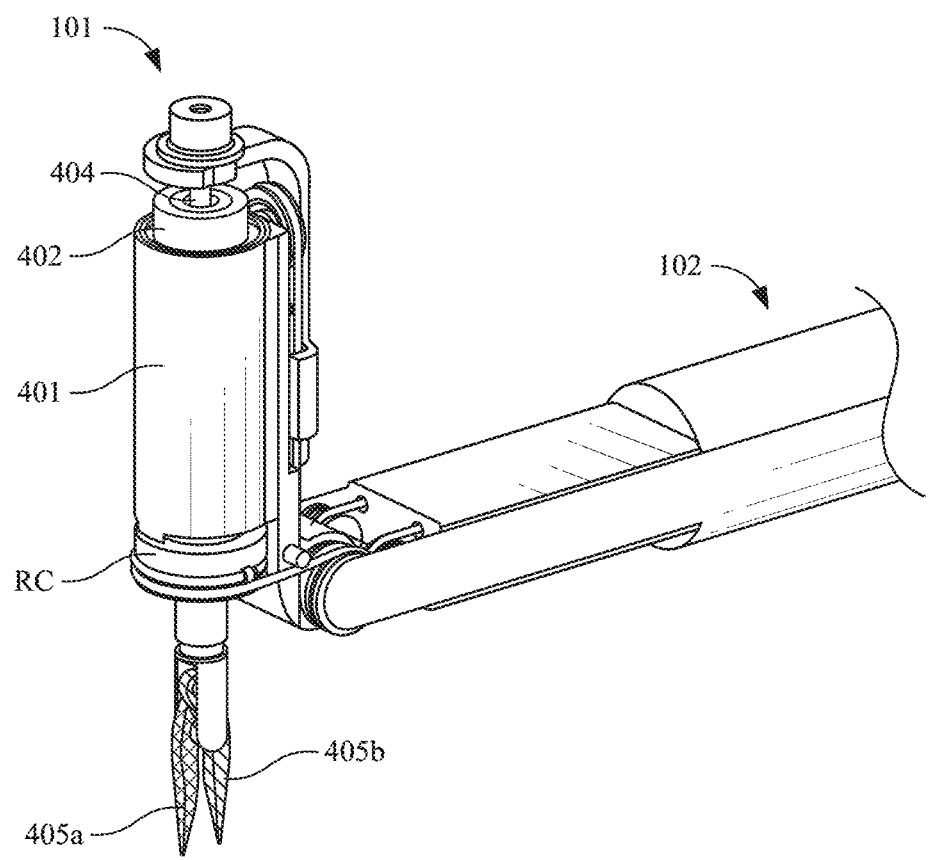
FIG. 5 is an enlarged view of the surgical tool unit end portion 101.
Figure 6:
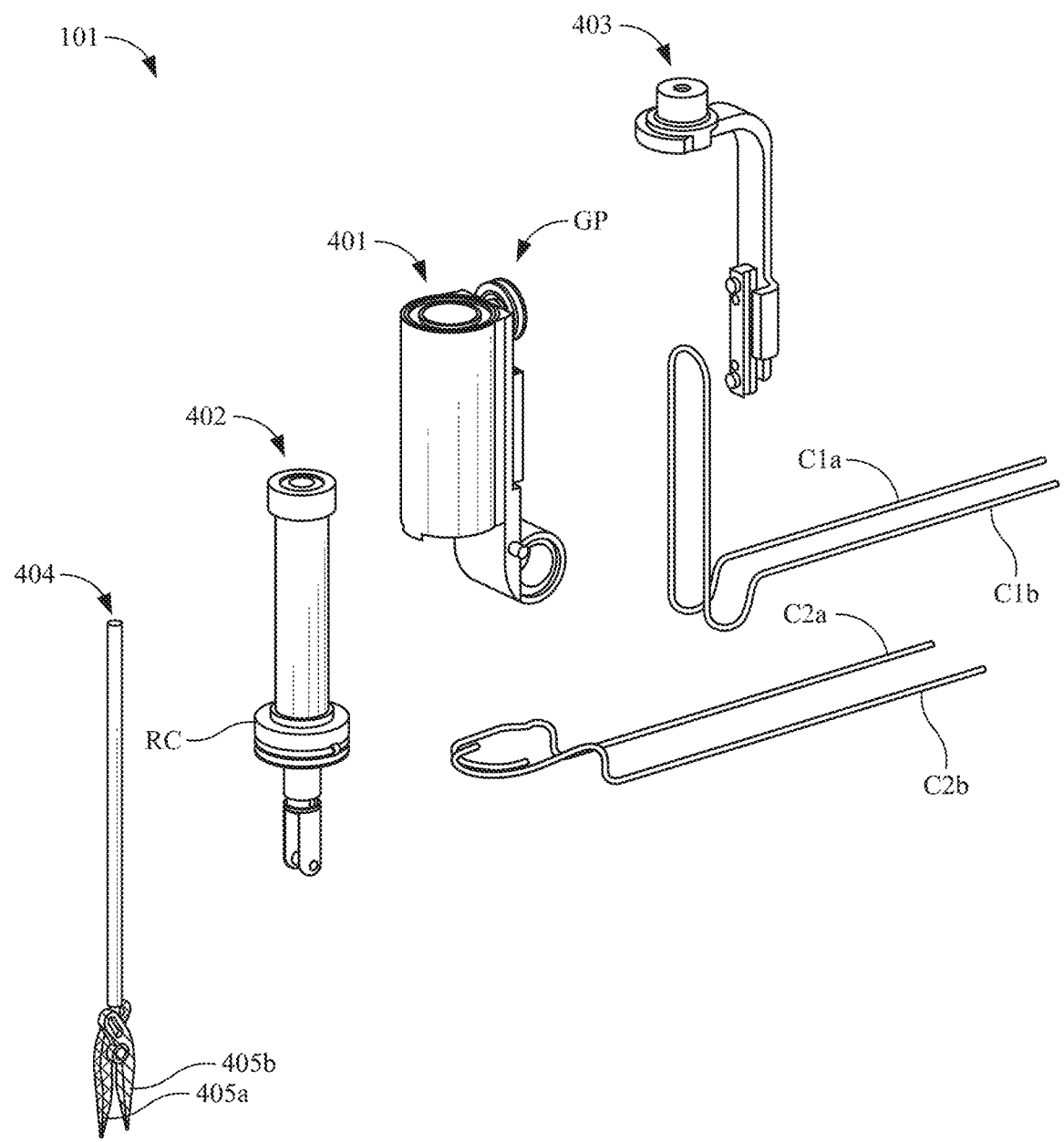
FIG. 6 is an exploded view of the surgical tool unit end portion 101.

FIGS. 4 and 5 show the surgical tool unit end portion 101 in an enlarged manner (however, the viewing direction is different between FIGS. 4 and 5). Further, FIG. 6 shows an exploded view of the surgical tool unit end portion 101. As shown in FIG. 6, the surgical tool unit end portion 101 includes a pitch unit 401, a roll unit 402, a grip unit 403, a rod 404, a pair of jaws 405a and 405b attached to the lower end of the rod 404, a set of first forward and backward cables C1a and C1b, and a set of second forward and backward cables C2a and C2b. For reference, in FIG. 7, the pitch unit 401 and the shaft 102 are shown in a transparent manner, and the layout of the respective cables in the vicinity of the surgical tool unit end portion 101 is made visible. Further, FIG. 8 shows a six-sided view of the surgical tool unit end portion 101. Note that the respective actuators for pulling the set of first forward and backward cables C1a and C1b, and the set of second forward and backward cables C2a and C2b are disposed in the surgical tool unit drive unit 103, but this aspect will be described later in detail.

As shown in FIG. 4, the pitch unit 401 is supported at a portion near the end of the shaft 102, so as to be able to turn about the first axis parallel to the pitch axis. As can be seen from FIGS. 6 and 7, the pitch unit 401 has a hollow cylindrical shape, with its rotation center being the second axis parallel to the roll axis. The roll unit 402 is then inserted into the hollow cylinder of the pitch unit 401. As a result, the roll unit 402 is supported by the pitch unit 401 so as to be able to rotate about the second axis. The roll unit 402 rotates about the second axis by the tractive force of the set of second forward and backward cables C2a and C2b, but this aspect will be described later in detail.

As shown in FIG. 4, a rail that restricts movement of the grip unit 403 is provided in the second axis direction on the back surface of the roll unit 402. Accordingly, the grip unit 403 can move in a predetermined range in the second axis direction (or the vertical direction) along the rail. The grip unit 403 moves in the second axis direction by the tractive force of the set of first forward and backward cables C1a and C1b, but this aspect will be described later in detail.

Figure 9:
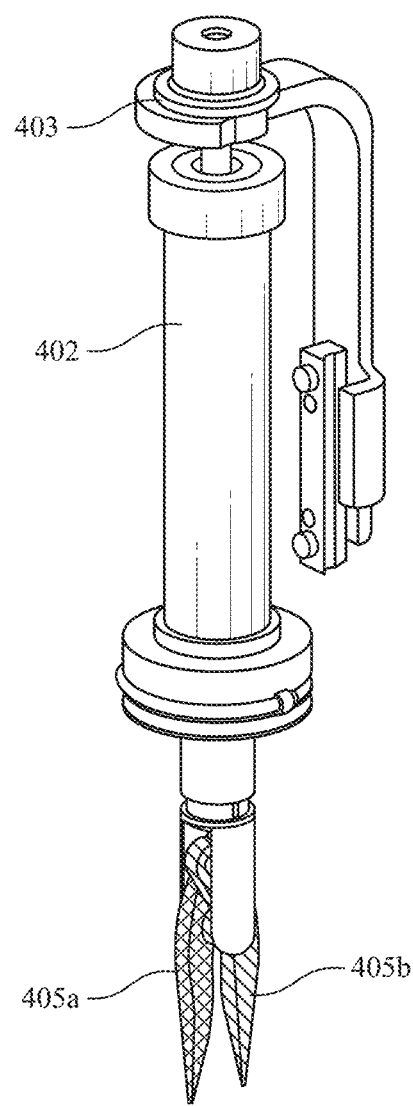
FIG. 9 is a diagram showing a roll unit 402, a grip unit, a rod 404, and a pair of jaws 405a and 405b.
Figure 10:
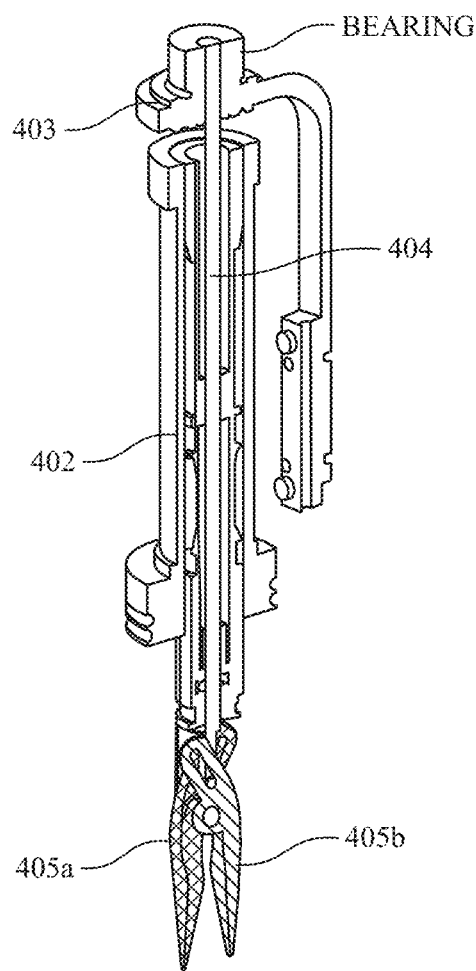
FIG. 10 is a diagram showing cross-sections of the roll unit 402, the grip unit, the rod 404, and the pair of jaws 405a and 405b.

FIG. 9 shows the roll unit 402, the grip unit, the rod 404, and the pair of jaws 405a and 405b, taken out from the surgical tool unit end portion 101. Further, FIG. 10 is a cross-sectional view of the roll unit 402, the grip unit, the rod 404, and the pair of jaws 405a and 405b, taken along a plane that is orthogonal to the first axis and includes the second axis.

The roll unit 402 has a through hole penetrating in the second axis direction, and the rod 404 is inserted into the through hole. The upper end portion of the rod 404 is supported by the grip unit 403 so as to be rotatable via a bearing. The bearing has a structure that supports a load applied in the second axis direction. The rod 404 is rotatable about the second axis with respect to the grip unit 403, but does not move in the second axis direction relative to the grip unit 403. Accordingly, when the grip unit 403 linearly moves in the second axis direction relative to the roll unit 402, the rod 404, together with the grip unit 403, also linearly moves in the second axis direction with respect to the roll unit 402.

Figure 11:
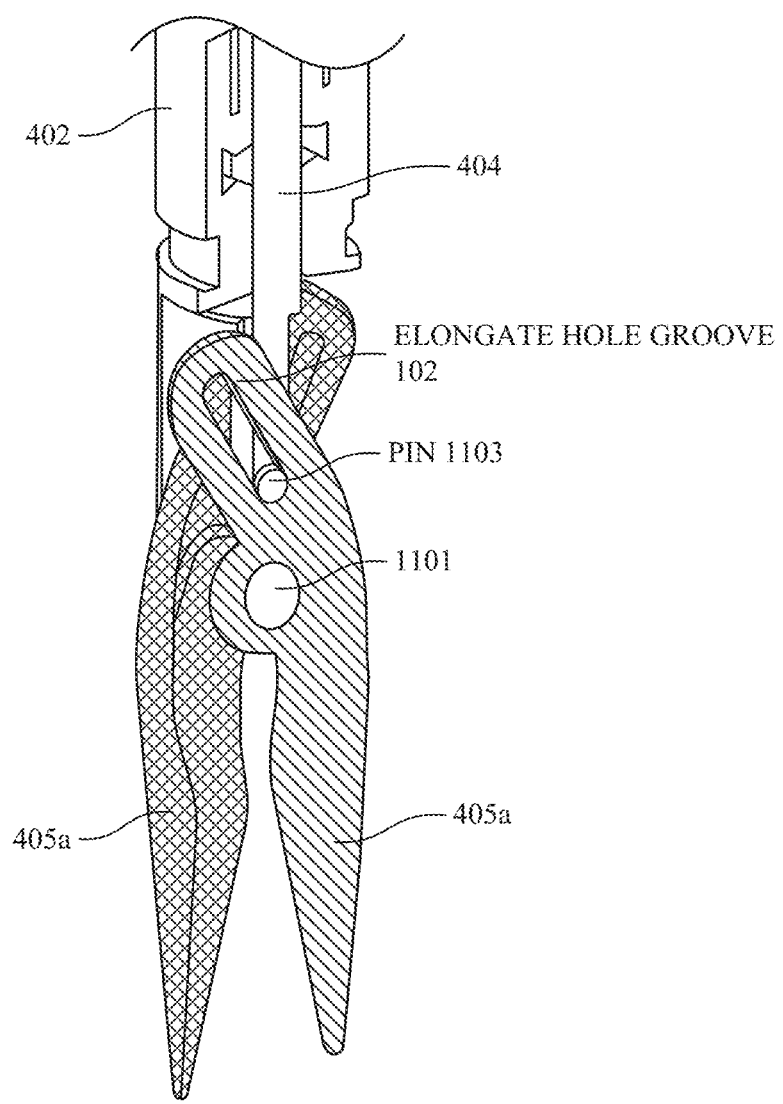
FIG. 11 is an enlarged cross-sectional view of the lower end of the rod 404 and the pair of jaws 405a and 405b.

FIG. 11 shows an enlarged cross-sectional view of the lower end of the rod 404 and the pair of jaws 405a and 405b.

The jaw 405a and the jaw 405b have shapes that are substantially symmetrical about the second axis. Both the jaw 405a and the jaw 405b are able to turn about an open-close shaft 1101 formed at the end of the roll unit 402. Also, in each of the jaws 405a and 405b, an elongate hole groove 1102 is formed behind the open-close shaft 1101. Further, a pin 1103 protruding from the end of the rod 404 is inserted into each of the elongate hole grooves 1102 of the jaws 405a and 405b. The longitudinal axes of the respective elongate hole grooves 1102 of the jaws 405a and 405b are inclined in opposite directions to each other with respect to the second axis, and a wall surface of each of the elongate grooves 1102 forms a cam that converts linear motion in the second axis direction into motion in the opening/closing direction of the jaws 405a and 405b.

As described above, the rod 404, together with the grip unit 403, linearly moves in the second axis direction with respect to the roll unit 402. The pin 1103 reciprocates in the second axis direction (which is the vertical direction of the paper surface), integrally with the rod 404. As the pin 1103 reciprocates so as to slide in each of the elongate groove holes 1102, the respective elongate groove holes 1102 need to cross the rod 404 (or the second axis) at the current position of the pin 1103. Also, the longitudinal axes of the respective elongate hole grooves 1102 of the jaws 405a and 405b are inclined in opposite directions to each other with respect to the second axis, and a wall surface of each of the elongate hole grooves 1102 forms a cam. Therefore, depending on linear motion of the pin 1103 in the second axis direction, the jaw 405a and the jaw 405b rotate in opposite directions to each other about the open-close shaft 1101. This is the mechanism in which the jaw 405a and the jaw 405b are opened and closed by linear motion of the rod 404 in the second axis direction. However, the open-close structure of the jaw 405a and the jaw 405b is not limited to this, and some other mechanism may be used to cause an opening and closing motion of the jaw 405a and the jaw 405b with linear motion of the rod 404 in the second axis direction.

Next, the mechanisms that use the tractive force of the cables to cause a turning motion of the pitch unit 401 about the first axis, a rotating motion of the roll unit 402 about the second axis, and an opening and closing motion of the jaws 405a and 405b are described in detail.

As shown in FIGS. 4 to 7, the surgical tool unit 100 includes the set of first forward and backward cables C1a and C1b, and the set of second forward and backward cables C2a and C2b. The respective actuators for pulling the set of first forward and backward cables C1a and C1b, and the set of second forward and backward cables C2a and C2b are disposed in the surgical tool unit drive unit 103, but this aspect will be described later in detail.

Figure 12:
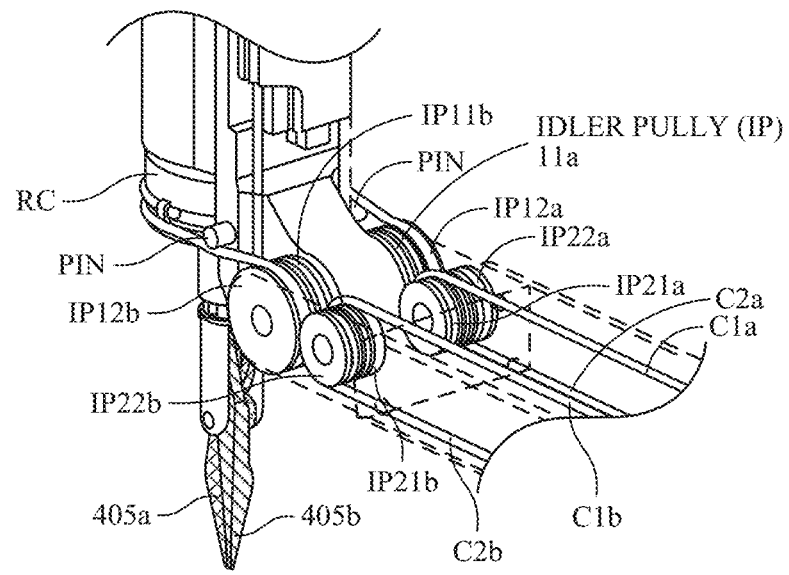
FIG. 12 is a diagram showing an enlarged view of a portion of the surgical tool unit end portion 101 in the vicinity of a first axis.
Figure 13:
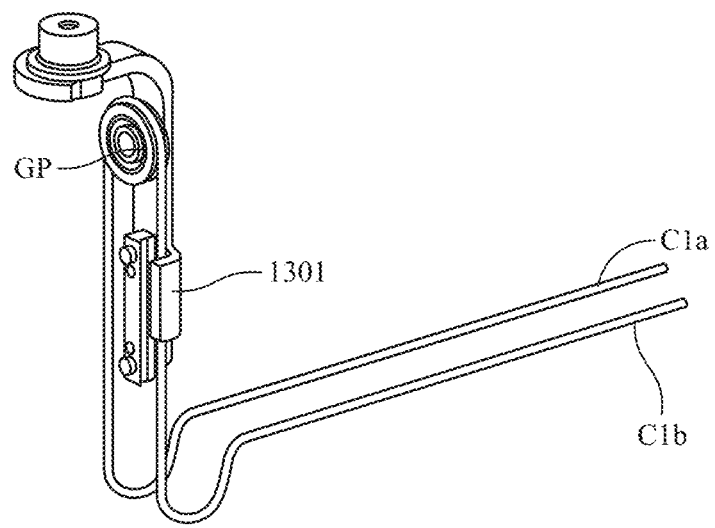
FIG. 13 is a diagram showing a mechanism in which a set of first forward and backward cables C1a and C1b is secured to the grip unit 403.
Figure 14:
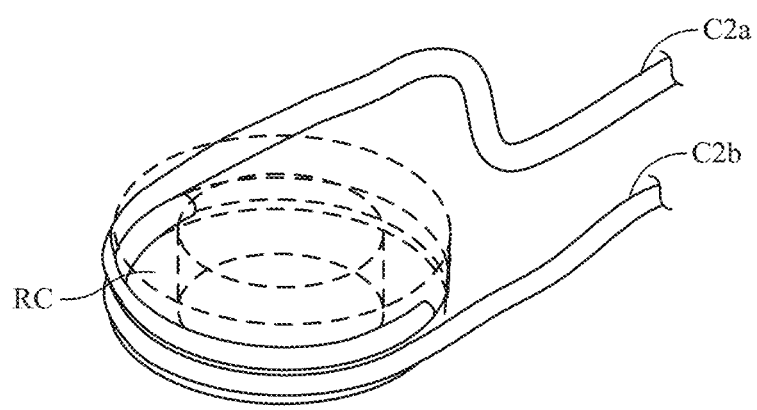
FIG. 14 is a diagram showing a mechanism in which a set of second forward and backward cables C2a and C2b is secured to the roll unit 402.

FIG. 12 is an enlarged view of a portion of the surgical tool unit end portion 101 through which the set of first forward and backward cables C1a and C1b, and the set of second forward and backward cables C2a and C2b pass in the vicinity of the first axis. Further, FIG. 13 shows a mechanism in which the set of first forward and backward cables C1a and C1b is secured to the grip unit 403. Further, FIG. 14 shows a mechanism in which the set of second forward and backward cables C2a and C2b is secured to the roll unit 402.

Referring to FIG. 13, the set of first forward and backward cables C1a and C1b is secured to the grip unit 403 at a cable connecting portion 1301 formed on in the grip unit 403. Referring to FIGS. 4, 6, and 13, the set of first forward and backward cables C1a and C1b is laid out, so as to be wound from opposite directions around a grip pulley GP rotatably supported on the back surface of the pitch unit 401, and to be folded back in a U-shape.

Further, referring to FIG. 12, the first forward cable C1a is pulled in the second axis direction. However, the direction of the cable C1a is switched to a direction orthogonal to the first axis by a first idler pulley IP11a that uses the first axis as its rotation axis, and further, the layout in the shaft 102 is adjusted so that the first forward cable C1a is inserted through the shaft 102 by a first adjacent idler pulley IP12a that is adjacent to the first idler pulley IP11a and has a rotation axis parallel to the first axis. Likewise, the first backward cable C1b is pulled in the second axis direction. However, the direction of the cable C1b is switched to a direction orthogonal to the first axis by a first idler pulley IP11b that uses the first axis as its rotation axis, and further, the layout is adjusted so that the first backward cable C1b is inserted through the shaft 102 by a first adjacent idler pulley IP12b that is adjacent to the first idler pulley IP11b and has a rotation axis parallel to the first axis.

After inserted through the shaft 102, the set of first forward and backward cables C1a and C1b is then pulled by an actuator disposed in the surgical tool unit drive unit 103. In this embodiment, the set of first forward and backward cables C1a and C1b is driven by a single motor (a first motor M1) by a cable loop method, which will be described in detail later. Alternatively, the first forward cable C1a and the first backward cable C1b can be designed to be pulled by individual motors.

The set of first forward and backward cables C1a and C1b is secured to the grip unit 403 at the cable connecting portion 1301 (described above). Accordingly, when the first forward cable C1a is pulled, the grip unit 403 ascends in the second axis direction along the rail (described above) on the back surface of the pitch unit 401. Also, when the first backward cable C1b is pulled, the grip unit 403 descends in the second axis direction. The rod 404 is supported by the grip unit 403 at the end portion (described above), and reciprocates in the second axis direction, together with the grip unit 403. Thus, a degree of freedom in opening and closing of the jaws 405a and 405b is achieved.

The roll unit 402 includes a roll capstan RC near the mid portion in the second axis direction. Referring to FIGS. 6 and 14, the second forward cable C2a and the second backward cable C2b are wound around the roll capstan RC from opposite directions to each other, and each of the cables is secured to the roll unit 402 at an end portion. Particularly, referring to FIG. 14, the second forward cable C2a and the second backward cable C2b are wound around the roll capstan RC so as to overlap each other by almost 180 degrees about the second axis. Thus, a range of ±150-degree movement of the roll unit 402 about the second axis is achieved.

Here, as shown in FIG. 12, in the pitch unit 401, pins protrude from portions near points through which the second forward cable C2a and the second backward cable C2b pass. The heights of the respective pins in the second axis direction are substantially the same. The second forward cable C2a is wound around the roll capstan RC after passing over the upper side of the pin, and the second backward cable C2b is wound around the roll capstan RC after passing under the pin. Accordingly, the second forward cable C2a and the second backward cable C2b are wound around the roll capstan RC, so as not to come into contact with each other while being separated from each other in the height direction of the second axis, but to overlap each other by almost 180 degrees about the second axis (see FIG. 14). As a result, when the roll unit 402 is driven by ±150 degrees about the second axis, the second forward cable C2a and the second backward cable C2b are not entangled.

Further, referring to FIG. 12, the second forward cable C2a is pulled in a direction orthogonal to the second axis direction. However, the direction of the cable C2a is switched to a direction orthogonal to the first axis by a second idler pulley IP21a that uses the first axis as its rotation axis, and further, the layout is adjusted so that the second forward cable C2a is inserted through the shaft 102 by a second adjacent idler pulley IP22a that is adjacent to the second idler pulley IP21a and has a rotation axis parallel to the first axis. Likewise, the second backward cable C2b is pulled in a direction orthogonal to the second axis direction. However, the direction of the cable C2b is switched to a direction orthogonal to the first axis by a second idler pulley IP21b that uses the first axis as its rotation axis, and further, the layout is adjusted so that the second backward cable C2b is inserted through the shaft 102 by a second adjacent idler pulley IP22b that is adjacent to the second idler pulley IP21b and has a rotation axis parallel to the first axis.

After inserted through the shaft 102, the set of second forward and backward cables C2a and C2b is then pulled by an actuator disposed in the surgical tool unit drive unit 103. In this embodiment, the set of second forward and backward cables C2a and C2b is driven by a single motor (a second motor M2) by a cable loop method, which will be described in detail later. Alternatively, the second forward cable C2a and the second backward cable C2b can be designed to be pulled by individual motors.

The second forward cable C2a and the second backward cable C2b are wound around the roll unit 402 from opposite directions to each other (described above). Accordingly, when the second forward cable C2a is pulled, the roll unit 402 can be made to rotate forward about the second axis. Also, when the second backward cable C2b is pulled, the roll unit 402 can be made to rotate in the reverse direction about the second axis. Thus, a rotational degree of freedom of the surgical tool unit end portion 101 about the second axis is achieved.

Figure 7:
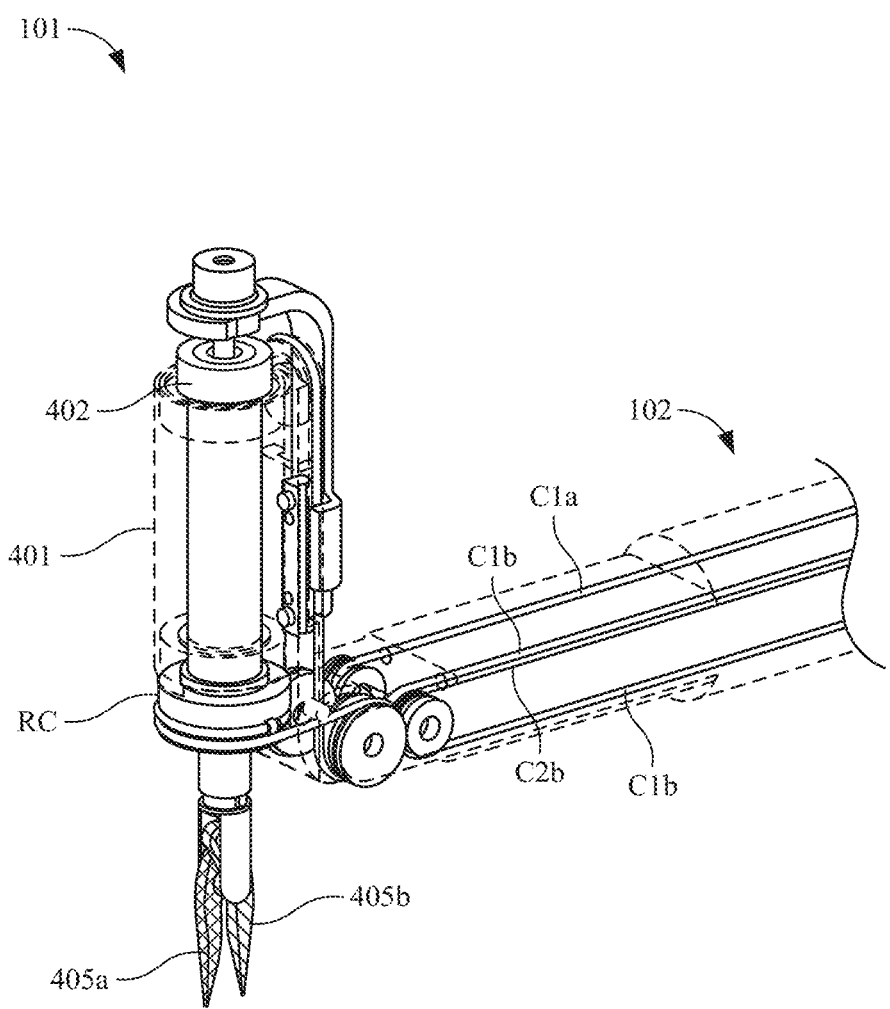
FIG. 7 is an enlarged view of the surgical tool unit end portion 101 (with a pitch unit 401 and a shaft 102 being illustrated in a transparent manner).
Figure 8:
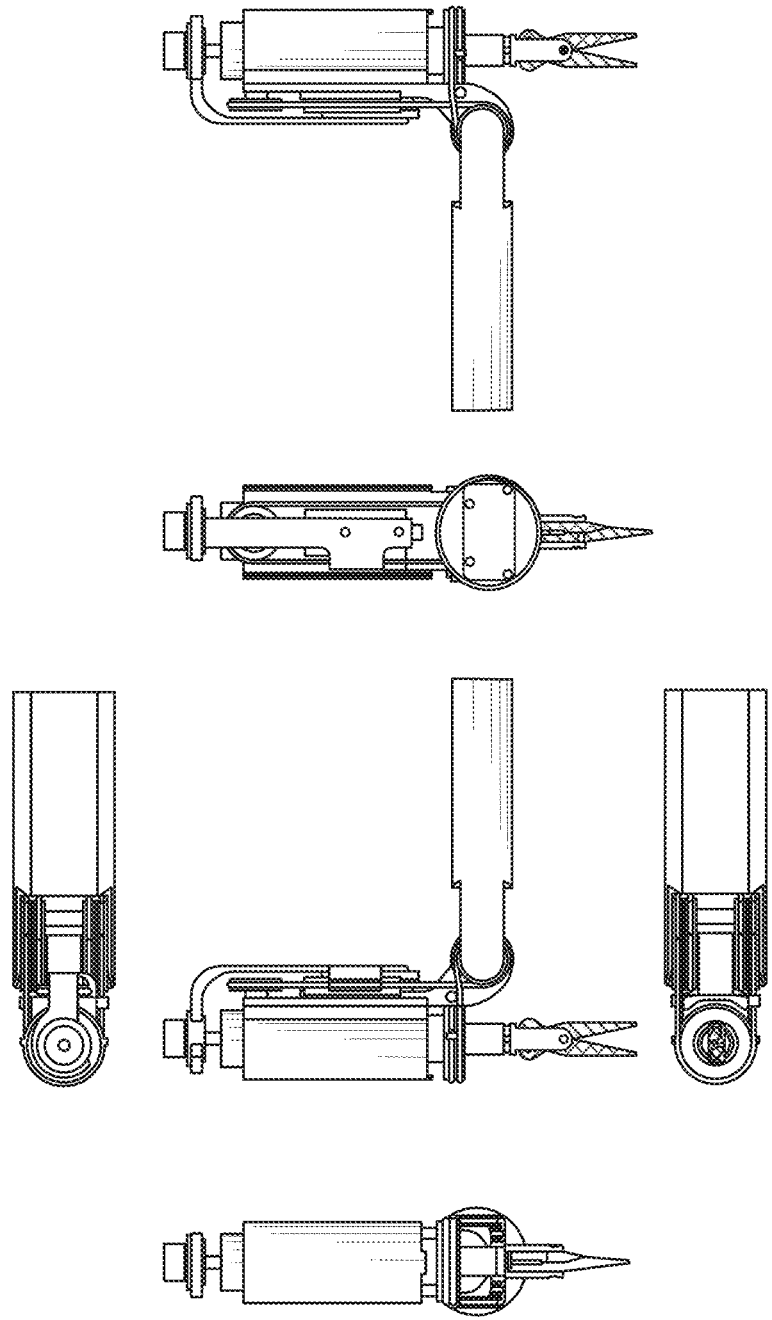
FIG. 8 is a six-sided view of the surgical tool unit end portion 101.

Note that, as can be seen from FIGS. 7 and 12, the idler pulleys IP11a, IP11b, IP21a, and IP21b all use the first axis as the rotation axis. Meanwhile, the adjacent idler pulleys IP12a, IP12b, IP22a, and IP22b all have the same rotation axis that is parallel to the first axis. Further, in the shaft 102, the layout is adjusted by the above respective idler pulleys so that the set of first forward and backward cables C1a and C1b passes on the upper side, and the set of second forward and backward cables C2a and C2b passes on the lower side.

Further, referring to FIGS. 4, 7, 12, and others, the set of second forward and backward cables C2a and C2b is wound around the idler pulleys IP21a and IP21b from the opposite direction to the direction in which the set of first forward and backward cables C1a and C1b is wound around the idler pulleys IP11a and IP11b. Therefore, when the set of first forward and backward cables C1a and C1b is pulled (or is moved backward in the longitudinal axis direction of the shaft 102) and when the set of second forward and backward cables C2a and C2b is moved backward, rotative forces in opposite directions about the first axis are applied to the pitch unit 401.

Accordingly, by selectively pulling one of the set of first forward and backward cables C1a and C1b and the set of second forward and backward cables C2a and C2b, it is possible to cause a turning motion of the pitch unit 401 about the first axis, and achieve a rotational degree of freedom of the surgical tool unit end portion 101 about the second axis.

C. Operations of a Surgical Tool Unit

Figure 15:
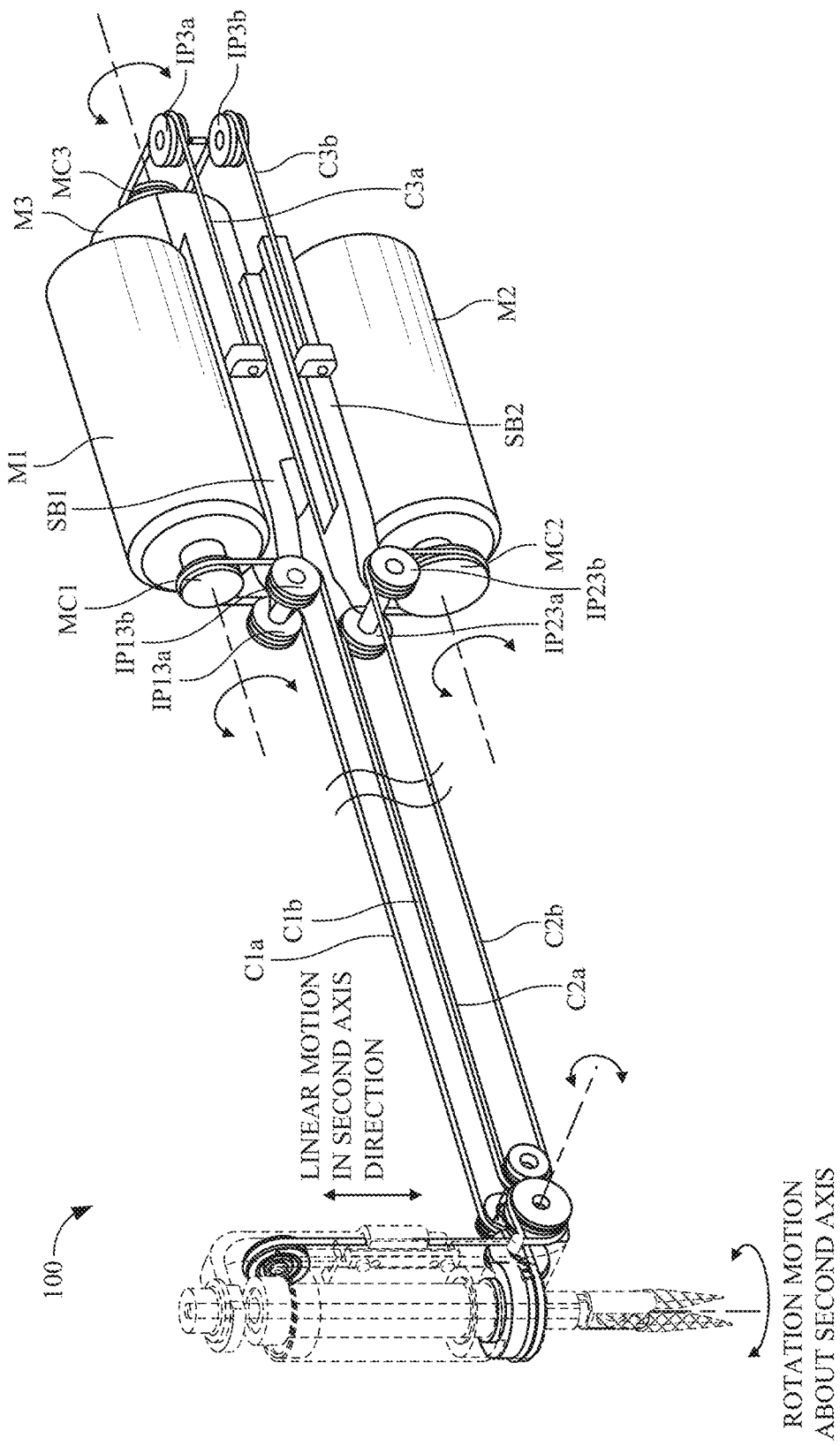
FIG. 15 is a diagram showing an example layout of actuators in a surgical tool unit drive unit 103.

FIG. 15 illustrates an example layout of the actuators in the surgical tool unit drive unit 103 and methods for pulling the cables with the respective actuators.

As shown in FIG. 15, a first motor M1, a second motor M2, and a third motor M3 are provided. Further, first to third motor capstans MC1, MC2, and MC3 as drive capstans are attached to the output shafts of the first to third motors M1 to M3, respectively.

Although a rotary motor is assumed to be used for each of the first to third motors M1 to M3 herein, a motor with a speed reducer may also be used. It is most preferable to use electromagnetic rotary motors as the first to third motors M1 to M3. However, it is also possible to use some other types of actuators capable of rotating the drive capstans.

The set of first forward and backward cables C1a and C1b is wound around the first motor capstan MC1 via idler pulleys IP13a and IP13b. The first motor M1 can rotate the first motor capstan MC1 in the positive direction, to apply a tractive force to the first forward cable set C1a. In this case, the grip unit 403 ascends relative to the pitch unit 401 and the roll unit 402. Accordingly, the rod 404 can also ascend in the second axis direction, and an operation to close the jaws 405a and 405b can be caused. Further, in a case where the first motor M1 rotates the first motor capstan MC1 in the negative direction to apply a tractive force to the first forward and backward cable set C1b, the grip unit 403 descends relative to the pitch unit 401 and the roll unit 402. Accordingly, the rod 404 also descends in the second axis direction, and an operation to open the jaws 405a and 405b can be caused. In short, the first motor M1 has a role to open and close the jaws 405a and 405b.

Figure 16:
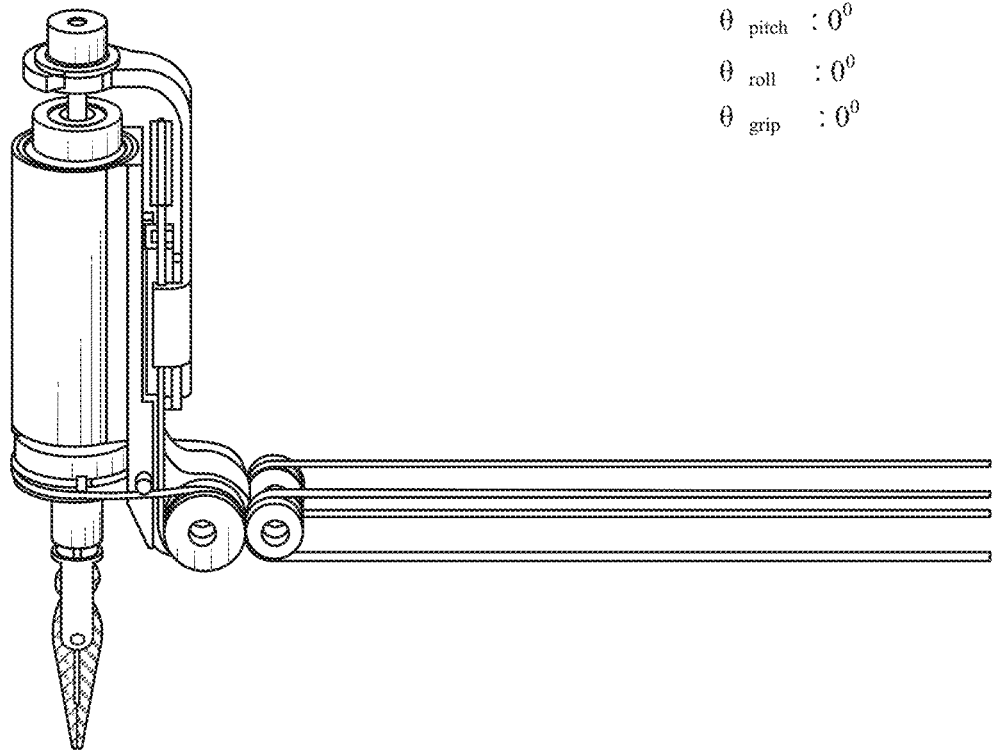
FIG. 16 is a diagram showing a state in which the jaws 405a and 405b open and close.
Figure 17:
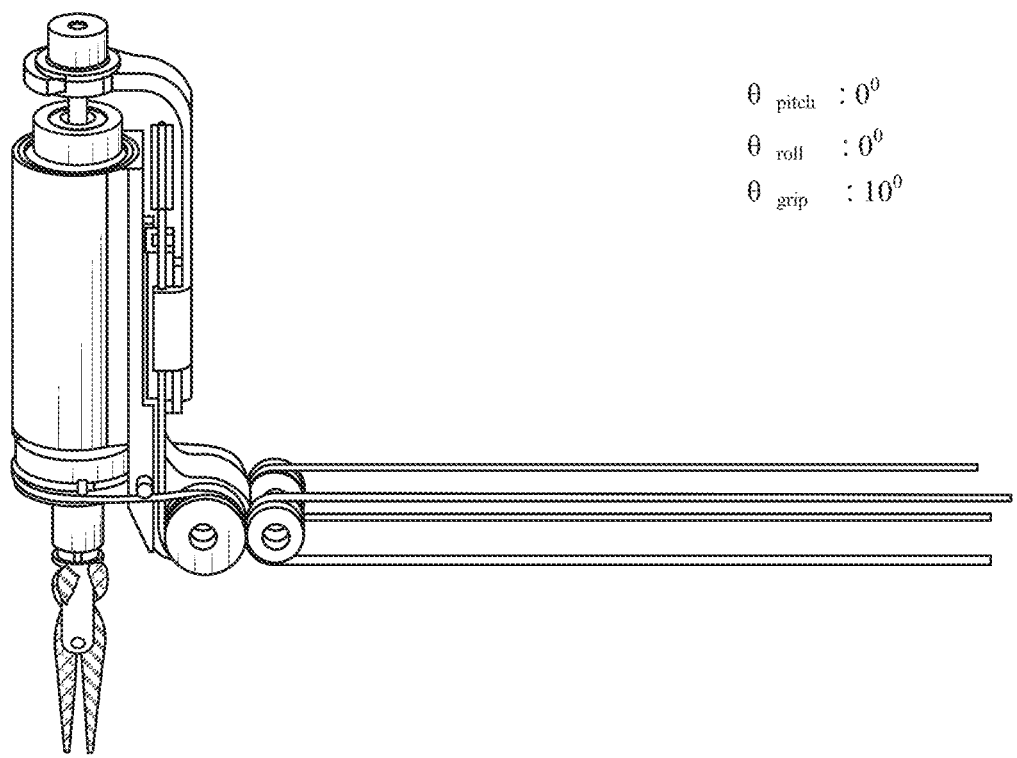
FIG. 17 is a diagram showing a state in which the jaws 405a and 405b open and close.
Figure 18:
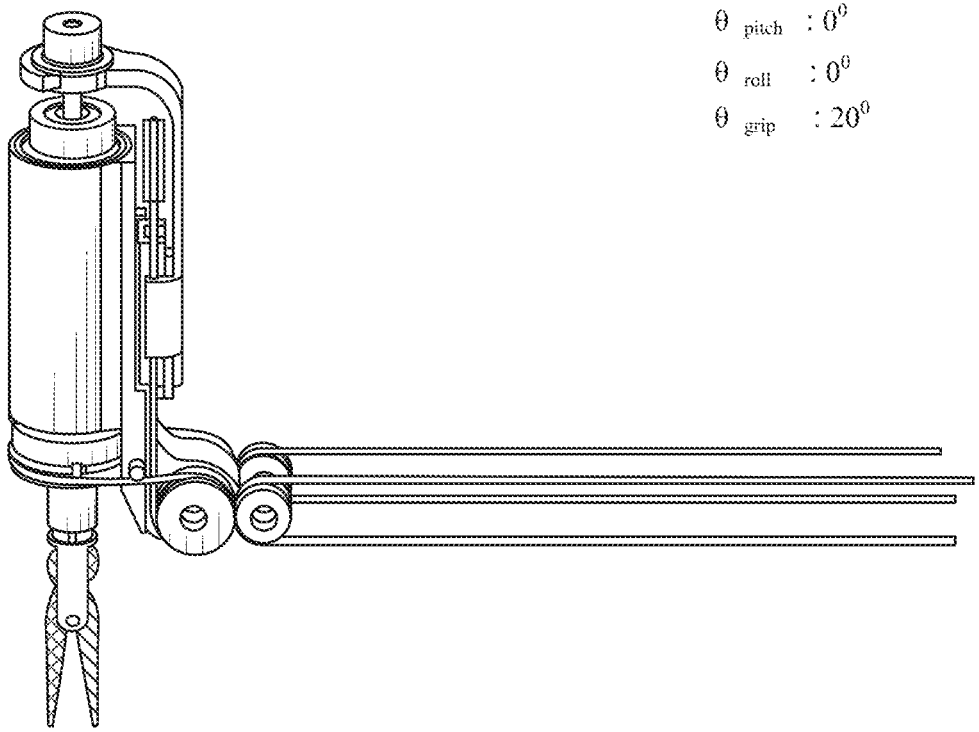
FIG. 18 is a diagram showing a state in which the jaws 405a and 405b open and close.
Figure 19:
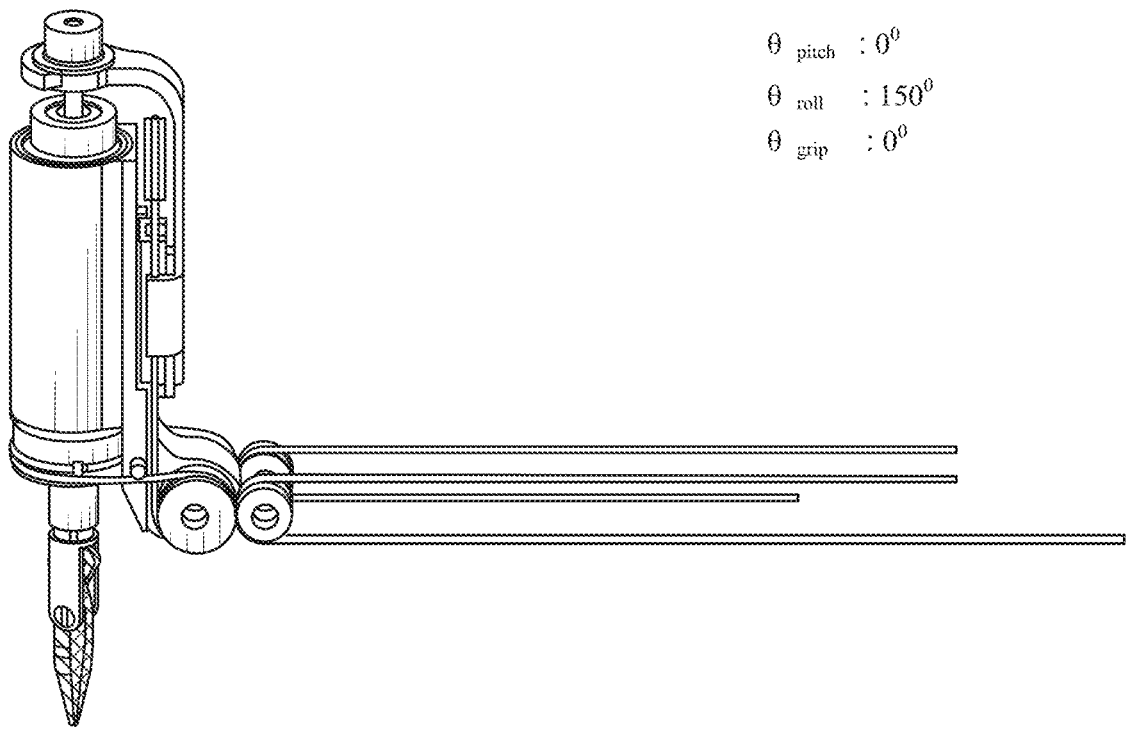
FIG. 19 is a diagram showing a state in which the roll unit 402 rotates about a second axis.
Figure 20:
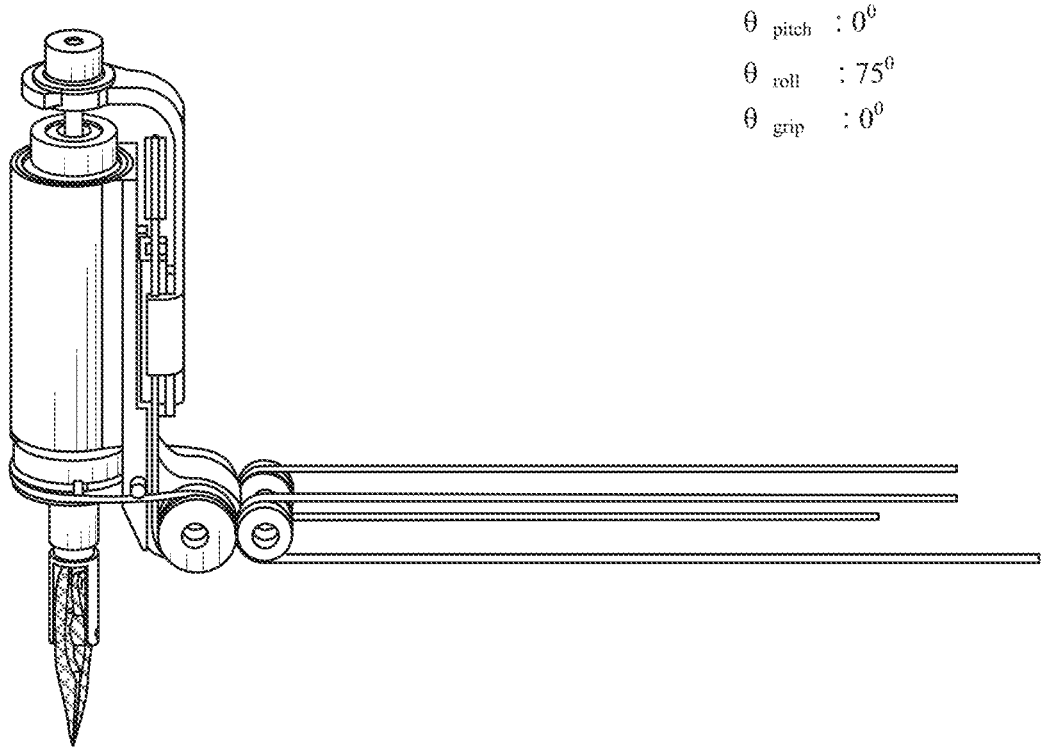
FIG. 20 is a diagram showing a state in which the roll unit 402 rotates about the second axis.
Figure 21:
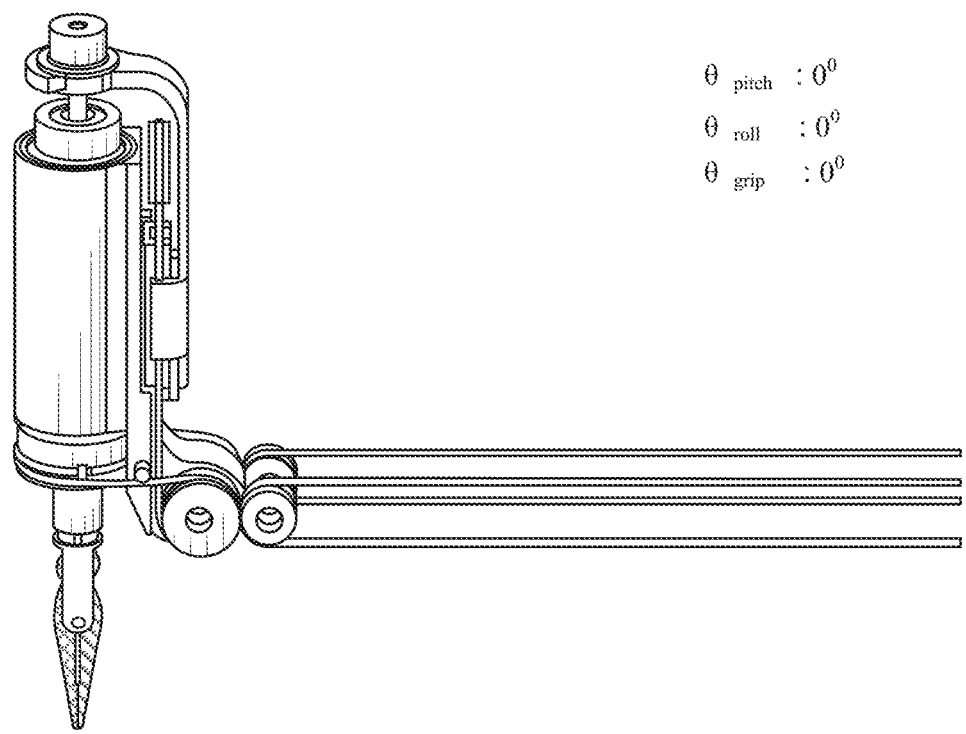
FIG. 21 is a diagram showing a state in which the roll unit 402 rotates about the second axis.
Figure 22:
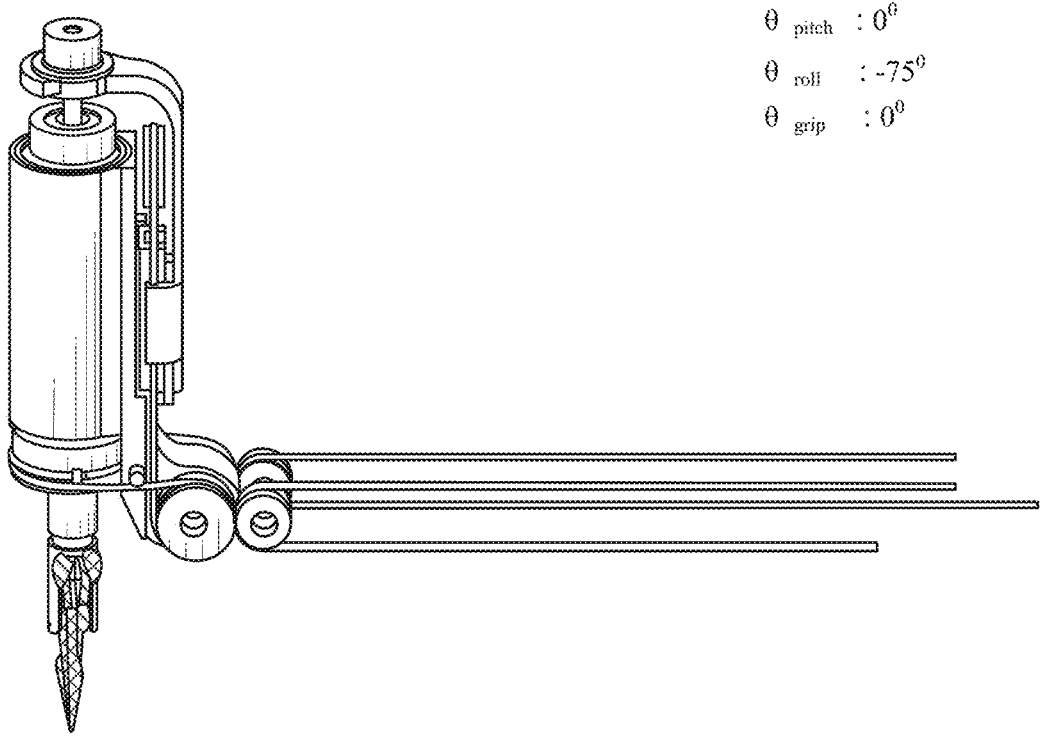
FIG. 22 is a diagram showing a state in which the roll unit 402 rotates about the second axis.
Figure 23:
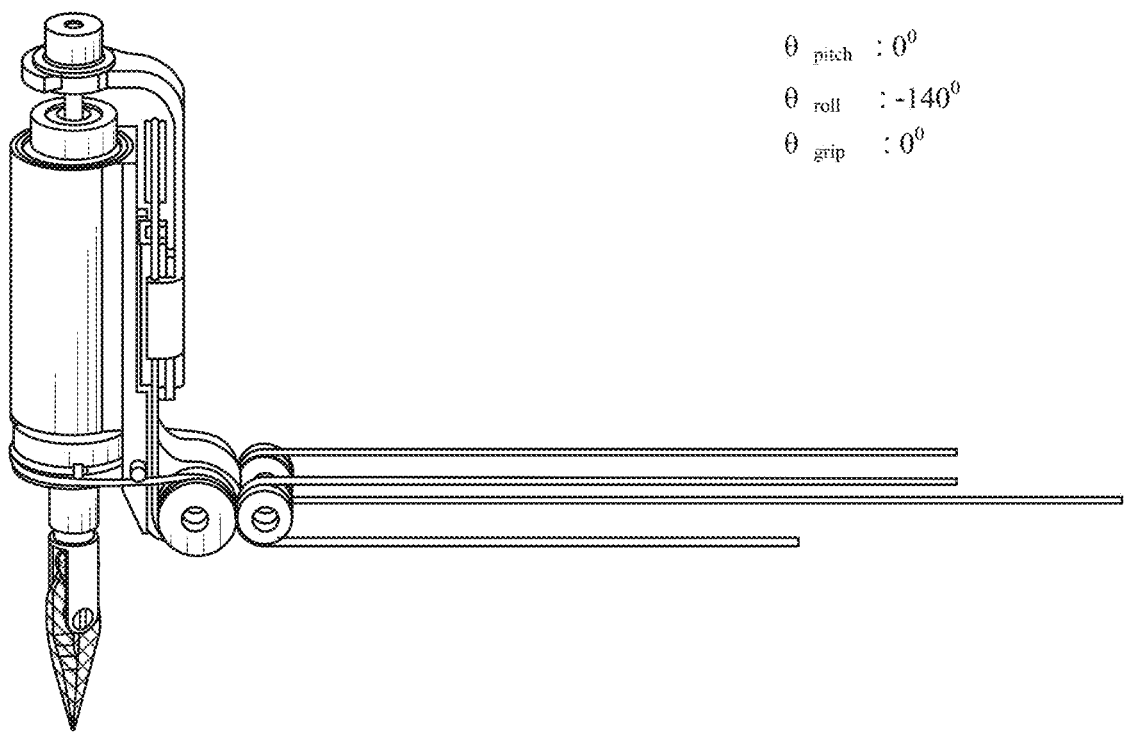
FIG. 23 is a diagram showing a state in which the roll unit 402 rotates about the second axis.
Figure 24:
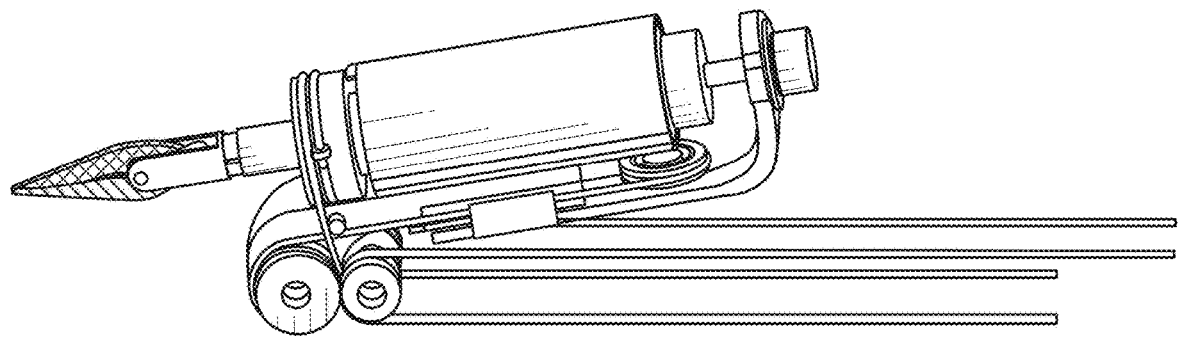
FIG. 24 is a diagram showing a state in which the pitch unit 401 turns about the first axis.

FIGS. 16 to 18 show a state in which the jaws 405a and 405b open and close. In an example shown in FIG. 16, the first motor capstan MC1 is maximally rotated in the positive direction by the first motor M1, and the grip unit 403 and the rod 404 are maximally raised by the tractive force of the first forward cable C1a, so that the jaws 405a and 405b are closed. Further, in an example shown in FIG. 17, the grip unit 403 and the rod 404 slightly descend, and the open angle of the jaws 405a and 405b is 10 degrees. Meanwhile, in an example shown in FIG. 18, the first motor capstan MC1 is maximally rotated in the negative direction by the first motor M1, and the grip unit 403 and the rod 404 are maximally lowered by the tractive force of the first backward cable C1b, so that the open angle between the jaws 405a and 405b is 20 degrees.

Further, referring to FIG. 15, the set of second forward and backward cables C2a and C2b is wound around the second motor capstan MC2 via idler pulleys IP23a and IP23b. Accordingly, when the second motor M2 rotates the second motor capstan MC2 in the positive direction to apply a tractive force to the second forward and backward cable set C2a, the roll unit 402 can be made to rotate in the positive direction about the second axis. Also, when the second motor M2 rotates the second motor capstan MC2 in the negative direction to apply a tractive force to the second forward and backward cable set C2a, the roll unit 402 can be made to rotate in the reverse direction about the second axis. In short, the second motor M2 has a role to rotate the roll unit 402 about the second axis parallel to the roll axis.

FIGS. 19 to 23 show a state in which the roll unit 402 rotates about the second axis. In an example shown in FIG. 19, the second motor capstan MC2 is maximally rotated in the positive direction by the second motor M2, and the roll unit 402 is rotated forward 150 degrees about the second axis by the tractive force of the second forward cable C2a. Meanwhile, in FIGS. 20 to 22, the second motor capstan MC2 is gradually rotated in the negative direction by the second motor M2, and the rotation angle of the roll unit 402 about the second axis is gradually reduced to 75 degrees, 0 degrees, and −75 degrees by the tractive force of the second backward cable C2b. Further, in an example shown in FIG. 23, the second motor capstan MC2 is maximally rotated in the negative direction by the second motor M2, and the roll unit 402 is rotated −140 degrees in the reverse direction about the second axis by the tractive force of the second forward cable C2b.

The third motor M3 has a role to rotate the pitch unit 401 about the first axis parallel to the pitch axis, but this aspect will be described later in detail.

As already mentioned, the set of second forward and backward cables C2a and C2b is wound around the idler pulleys IP21a and IP21b from the opposite direction to the direction in which the set of first forward and backward cables C1a and C1b is wound around the idler pulleys IP11a and IP11b. Therefore, when the set of first forward and backward cables C1a and C1b is pulled (or is moved backward in the longitudinal axis direction of the shaft 102) and when the set of second forward and backward cables C2a and C2b is moved backward, rotative forces in opposite directions about the first axis are applied to the pitch unit 401.

Accordingly, by selectively pulling one of the set of first forward and backward cables C1a and C1b and the set of second forward and backward cables C2a and C2b, it is possible to cause a turning motion of the pitch unit 401 about the first axis, and achieve a rotational degree of freedom of the surgical tool unit end portion 101 about the second axis.

Referring to FIG. 15, the first motor M1 is supported on a first slide base SB1 that slides in the longitudinal axis direction of the shaft 102, and the second motor M2 is supported on a second slide base SB2 that slides in the longitudinal axis direction of the shaft 102. Further, a set of third forward and backward cables C3a and C3b is wound around the third motor capstan MC3 via third idler pulleys IP3a and IP3b. The other end of the third forward cable C3a is then secured to the first slide base SB1, and the other end of the third backward cable C3b is secured to the second slide base SB2.

Accordingly, the third motor M3 can rotate the third motor capstan MC3 in the positive direction, to apply a tractive force to the third forward cable C3a. In this case, the first slide base SB1 moves backward to the root side (which is the proximal end) of the shaft 102, and the second slide base SB2 moves forward to the end side (which is the distal end) of the shaft 102. The set of first forward and backward cables C1a and C1b then moves backward, and the set of second forward and backward cables C2a and C2b moves forward. As a result, the pitch unit 401 rotates in the positive direction about the first axis.

Conversely, the third motor M3 can rotate the third motor capstan MC3 in the negative direction, to apply a tractive force to the third backward cable C3b. In this case, the second slide base SB2 moves backward to the root side (which is the proximal end) of the shaft 102, and the first slide base SB1 moves forward to the end side (which is the distal end) of the shaft 102. The set of first forward and backward cables C1a and C1b then moves forward, and the set of second forward and backward cables C2a and C2b moves backward. As a result, the pitch unit 401 rotates in the negative direction about the first axis.

FIGS. 24 to 28 show a state in which the pitch unit 401 turns about the first axis. In an example shown in FIG. 24, the third motor M3 rotates maximally in the positive direction, and the first slide base SB1 is maximally moved backward by the tractive force of the third forward cable C3a. As a result, the pitch unit 401 turns 80 degrees about the first axis.

Figure 25:
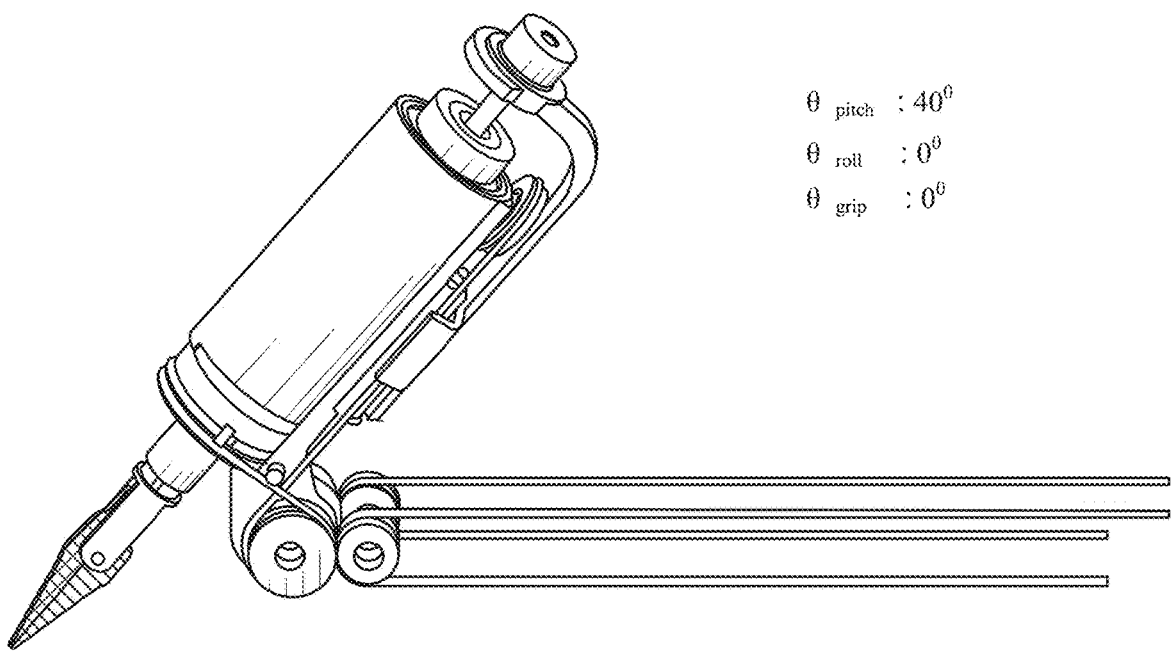
FIG. 25 is a diagram showing a state in which the pitch unit 401 turns about the first axis.
Figure 26:
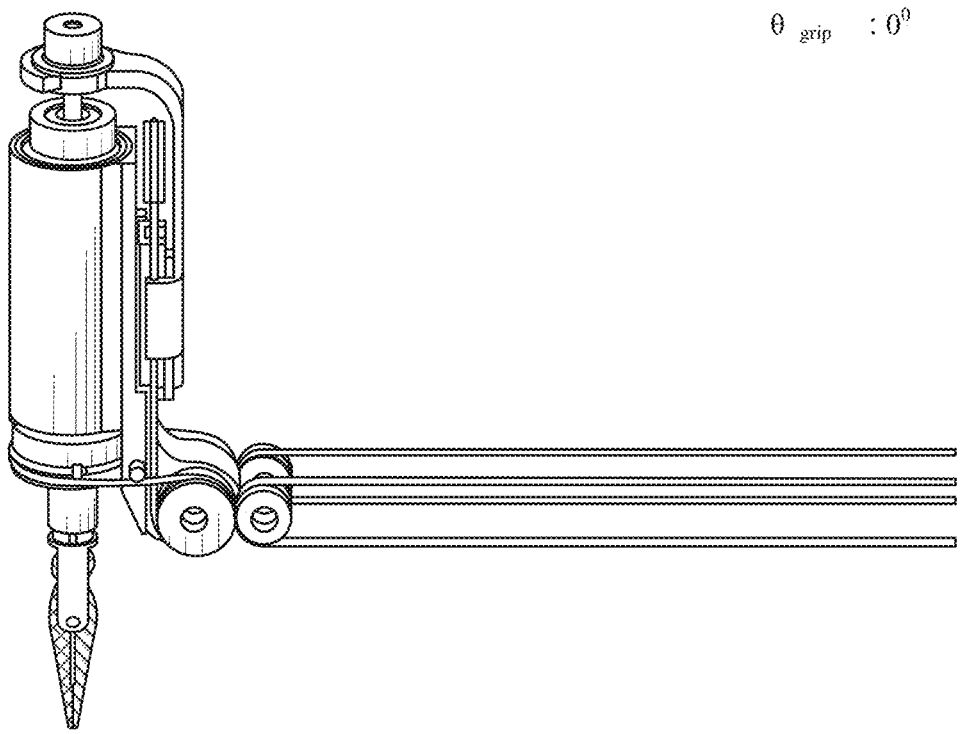
FIG. 26 is a diagram showing a state in which the pitch unit 401 turns about the first axis.
Figure 27:
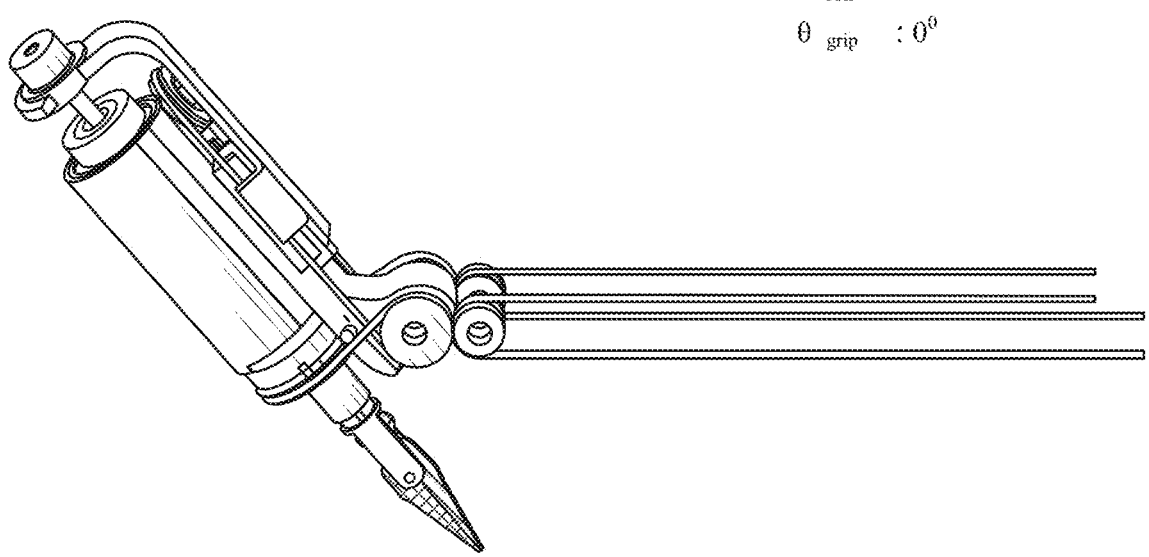
FIG. 27 is a diagram showing a state in which the pitch unit 401 turns about the first axis.

Meanwhile, in FIGS. 25 to 27, the third motor capstan MC3 is gradually rotated in the negative direction by the third motor M3, and the second slide base SB2 is gradually moved backward by the tractive force of the third backward cable C3b. As a result, the pitch unit 401 gradually turns in the negative direction about the first axis, and the turning angle gradually decreases to 40 degrees, 0 degrees, and −40 degrees.

Figure 28:
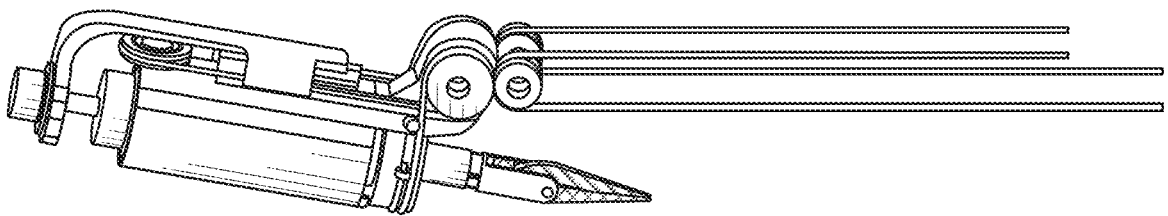
FIG. 28 is a diagram showing a state in which the pitch unit 401 turns about the first axis.

Further, in an example shown in FIG. 28, the third motor M3 rotates maximally in the negative direction, and the second slide base SB2 is maximally moved backward by the tractive force of the third backward cable C3b. As a result, the pitch unit 401 turns −80 degrees about the first axis.

Furthermore, in the surgical tool unit end portion 101, the turning motion of the pitch unit 401 about the first axis, the rotating motion of the roll unit 402 about the second axis, and the gripping motion of the pair of jaws 405a and 405b (or the linear motion of the grip unit 403 in the second axis direction) do not interfere with one another, and the three axes can be simultaneously driven.

Figure 29:
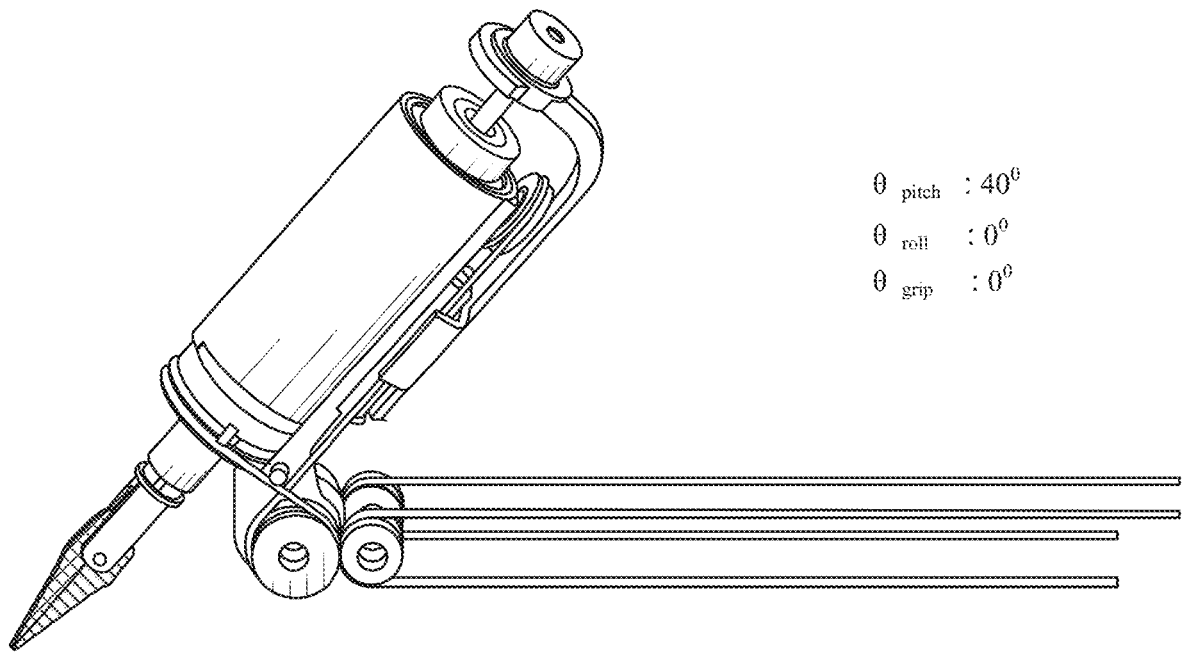
FIG. 29 is a diagram showing a state in which three axes are simultaneously driven in the surgical tool unit end portion 101.
Figure 30:
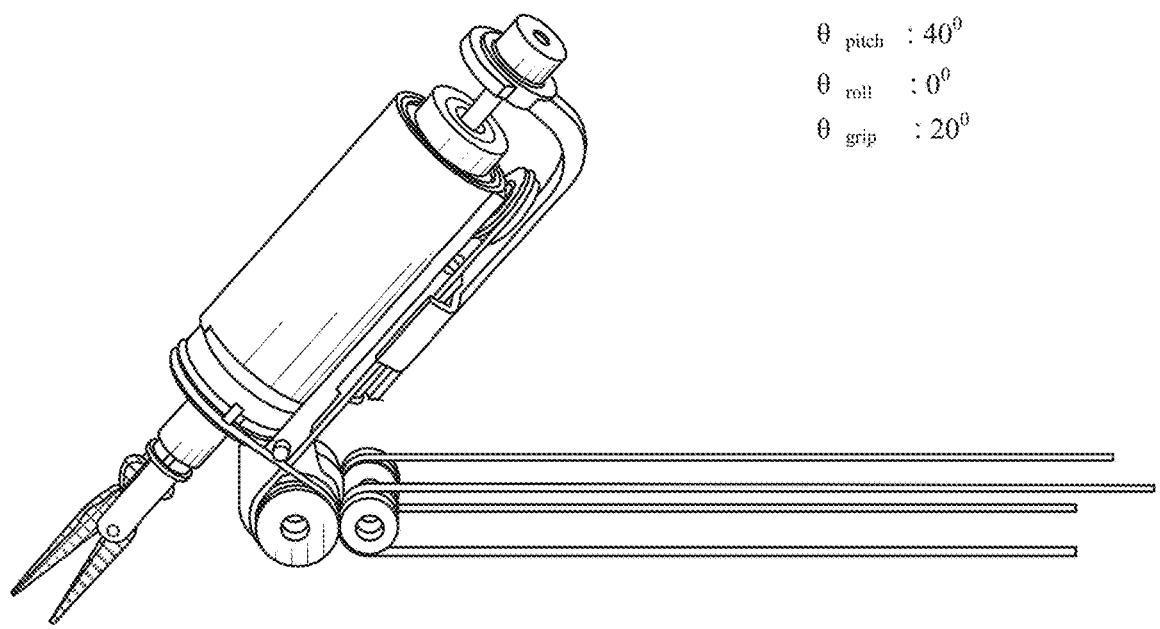
FIG. 30 is a diagram showing a state in which three axes are simultaneously driven in the surgical tool unit end portion 101.
Figure 31:
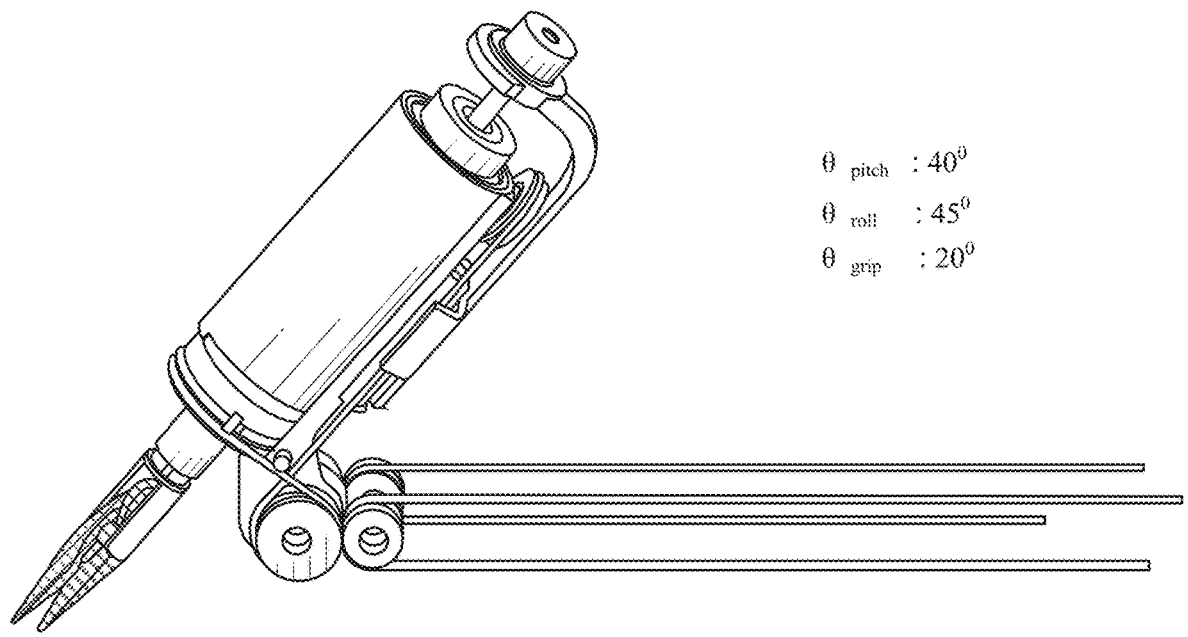
FIG. 31 is a diagram showing a state in which three axes are simultaneously driven in the surgical tool unit end portion 101.

FIGS. 29 to 31 show a state in which the three axes are simultaneously driven in the surgical tool unit end portion 101.

In an example shown in FIG. 29, the third motor capstan MC3 is rotated in the positive direction by the third motor M3, and the first slide base SB1 is moved backward by the tractive force of the third forward cable C3a, so that the pitch unit 401 is made to turn 40 degrees about the first axis.

Meanwhile, in an example shown in FIG. 30, in a state where the pitch unit 401 has turned 40 degrees about the first axis, the jaws 405a and 405b are further opened up to an open angle of 20 degrees. In this case, the first motor M1 rotates the first motor capstan MC1 in the negative direction, to pull the first backward cable set C1b. As a result, the rod 404 descends in the second axis direction, and thus, an opening motion of the jaws 405a and 405b is caused.

Further, in an example shown in FIG. 31, in a state where the pitch unit 401 has turned 40 degrees about the first axis, and the jaws 405a and 405b are opened up to an open angle of 20 degrees, the roll unit 402 is further made to turn 45 degrees about the second axis in the positive direction. In this case, the second motor capstan MC2 is rotated in the positive direction by the second motor M2, and the operation in which the roll unit 402 rotates forward 45 degrees about the second axis is caused by the tractive force of the second forward cable C2a.

The operation methods in the surgical tool unit end portion 101 are summarized below.

Operation at the First Axis

When the third motor capstan MC3 is rotated by the third motor M3, a tractive force is generated in one cable of the set of third forward and backward cables C3a and C3b, and the first slide base SB1 and the second slide base SB2 can be moved forward and backward in the longitudinal axis direction of the shaft 102. As a result, one of the set of first forward cables C1a and C1b, and the set of second forward and backward cables C2a and C2b moves forward, and the other moves backward. Accordingly, the pitch unit 401 can be made to turn in the positive direction or the reverse direction about the first axis, as shown in FIGS. 24 to 28.

Operation at the Second Axis

When the second motor capstan MC2 is rotated by the second motor M2, a tractive force is generated in one cable of the set of second forward and backward cables C2a and C2b, and the roll unit 402 can be made to rotate in the positive direction and the reverse direction about the second axis. As a result, a rotating operation of the grip unit 403 about the second axis is caused.

Gripping Operation

The jaws 405a and 405b are able to turn about the open-close shaft 1101 formed at the end of the roll unit 402, and turn about the open-close shaft 1101 in opposite directions to each other in accordance with linear motion of the rod 404 in the second axis direction. When the first motor capstan MC1 is rotated by the first motor M1, a tractive force is then generated in one cable of the set of first forward and backward cables C1a and C1b, to raise or lower the rod 404 in the second axis direction. Thus, an opening and closing operation of the jaws 405a and 405b is caused.

Next, the relationship between operations of the first to third motors M1 to M3 and operations of the surgical tool unit end portion 101 is described.

Figure 32:
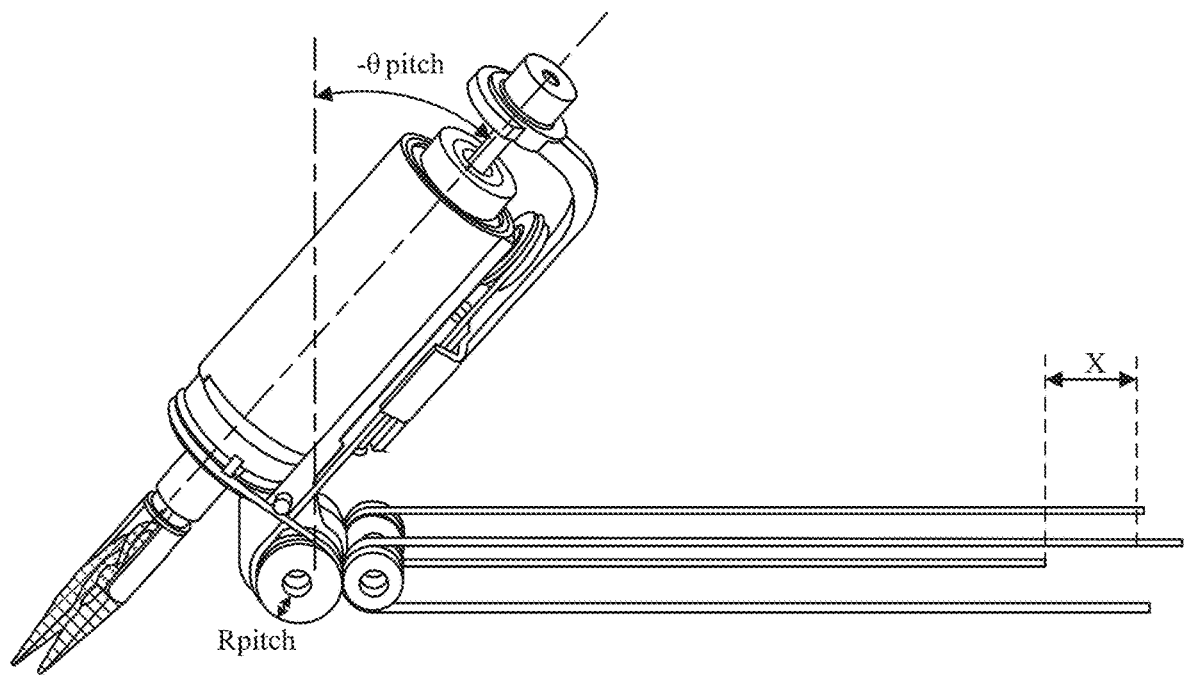
FIG. 32 is a diagram showing an example operation in which the pitch unit 401 rotates about the first axis.

FIG. 32 shows an example operation in which the pitch unit 401 turns about the first axis. Here, the drawing is a view of the surgical tool unit end portion 101 as viewed from a direction parallel to the first axis. As shown in the drawing, the radius of each of the idler pulleys P11a, P11b, P21a, and P21b using the first axis as the rotation axis is represented by $R_{pitch}$, and the turning angle of the pitch unit 401 about the first axis is $\theta_{pitch}$. Further, the amount of displacement of a cable from a predetermined reference position in the longitudinal axis direction of the shaft 102 is represented by X.

Figure 33:
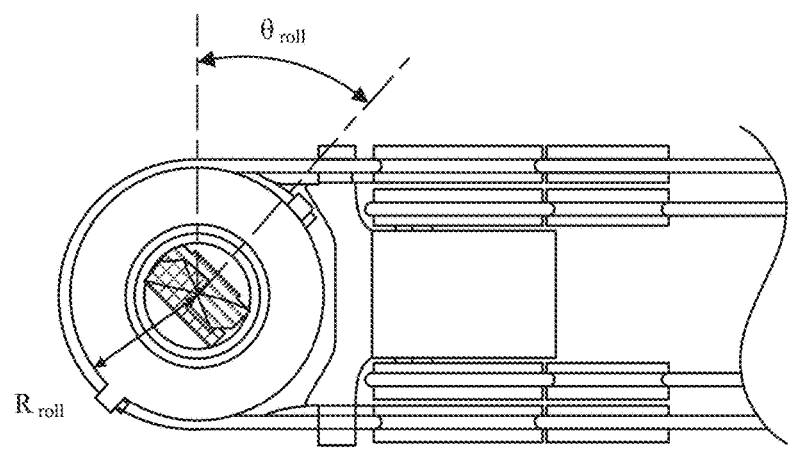
FIG. 33 is a diagram showing an example operation in which the roll unit 402 rotates about the second axis.

Further, FIG. 33 shows an example operation in which the roll unit 402 (or the jaws 405a and 405b) rotates about the second axis. Here, the drawing is a view of the surgical tool unit end portion 101 as viewed from a direction parallel to the second axis. As shown in the drawing, the pulley radius of the roll capstan RC is represented by $R_{roll}$, and the angle of rotation of the roll unit 402 about the second axis is $\theta_{roll}$.

Figure 34:
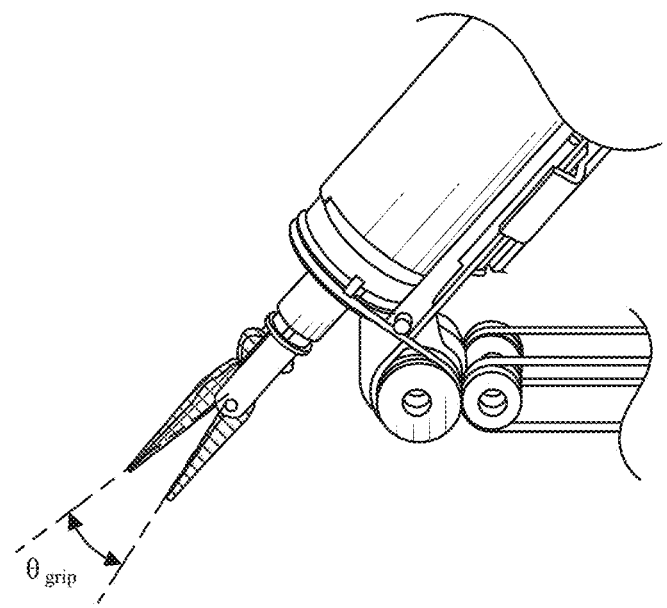
FIG. 34 is a diagram showing an example gripping operation of the jaws 405a and 405b.

Further, FIG. 34 shows an example gripping operation in which the jaws 405a and 405b turn about the open-close shaft to open and close. Here, the drawing is a view of the surgical tool unit end portion 101 as viewed from a direction parallel to the first axis. As already described with reference to FIG. 11, the jaws 405a and 405b open and close in accordance with linear motion of the rod 404 in the second axis direction. The open angle of the jaws 405a and 405b is represented by $\theta_{grip}$.

Figure 35:
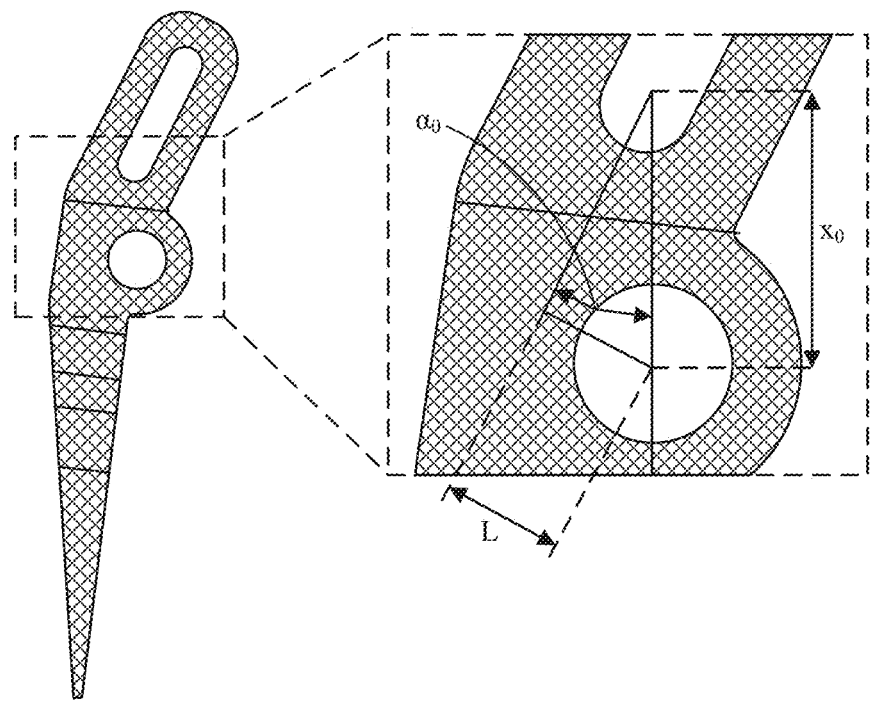
FIG. 35 is a diagram showing an example turning operation of a jaw.

FIG. 35 shows a positional relationship between the open-close shaft of the jaws and the pin that is provided at the end of the rod 404 and slides in the elongate groove holes formed in the jaws. In FIG. 35, the left side shows an entire jaw, and the right side shows the portion near the open-close shaft in an enlarged manner. Note that, although an example of the jaw 405a is shown in the drawing, the same applies to the jaw 405b. The drawing shows a state in which the jaws 405a and 405b are closed. Where the jaws 405a and 405b are closed, the distance from the center of the open-close shaft to the pin at the end of the rod 404 (not shown in FIG. 35) is represented by $x_0$, and the inclination angle of the long axis of the elongate groove hole with respect to the second axis is $\alpha_0$. Further, L represents the height of a right triangle whose oblique side is a line segment of the distance $x_0$ connecting the center of the open-close shaft to the pin at the end of the rod 404.

Figure 36:
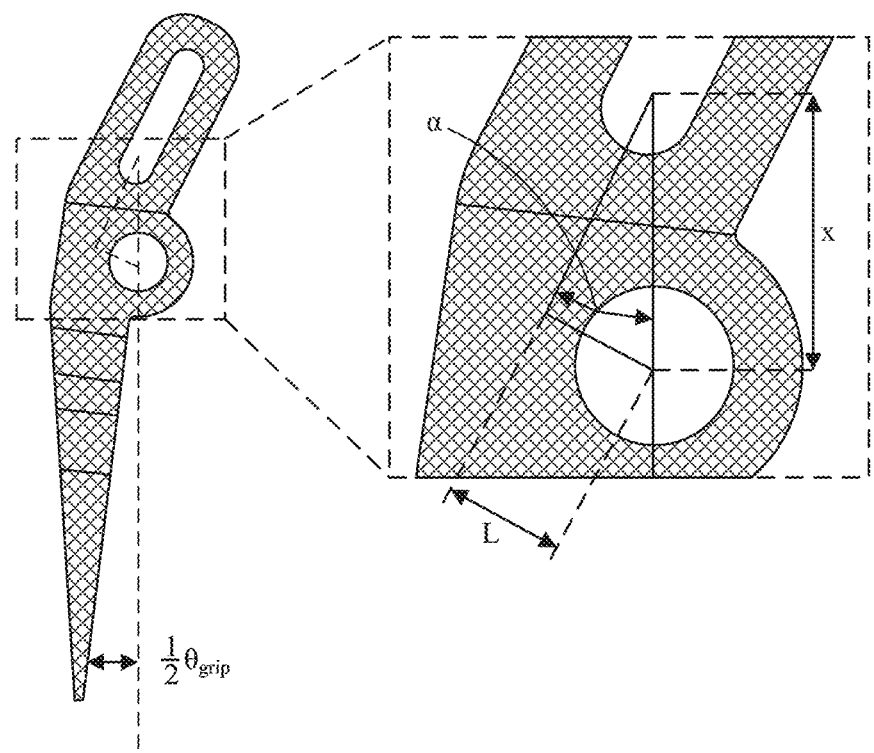
FIG. 36 is a diagram showing an example turning operation of a jaw.

The wall surface of the long groove hole formed in the jaw forms a cam surface, and the pin at the end of the rod 404 slides along the wall surface of the elongate groove hole. As described above, when the grip unit 403 ascends, and the rod 404 also ascends in the second axis direction, an operation to close jaws 405a and 405b is performed. Conversely, when the grip unit 403 descends, and the rod 404 also descends in the second axis direction, an operation to open the jaws 405a and 405b is performed. FIG. 36 shows a state in which the rod 404 (not shown in FIG. 36) descends in the second axis direction, and the distance from the center of the open-close shaft to the pin at the end of the rod 404 changes from $x_0$ to x. In FIG. 36, the left side shows an entire jaw, and the right side shows the portion near the open-close shaft in an enlarged manner. The open angle of the jaw at this point of time is represented by $\theta_{grip}/2$, and the inclination angle of the long axis of the elongate groove hole with respect to the second axis is $\alpha$. Further, L represents the height of a right triangle having an oblique side of the distance x between the center of the open-close shaft and the pin at the end of the rod 404. At this point of time, displacement ($x_0$-x) of the rod 404 in the second axis direction is expressed as in Equation (1) shown below.

[Mathematical Formula 1]

$$x_0 - x = \frac{L}{\sin(\alpha_0)} - \frac{L}{\sin\left(\frac{1}{2}\theta_{grip} + \alpha_0\right)} \quad (1)$$

Referring back to FIGS. 32 to 34, explanation is continued. Each of the set of first forward and backward cables C1a and C1b, and the set of second forward and backward cables C2a and C2b is moved forward and backward in the longitudinal axis direction of the shaft 102 by drive of the first to third motors M1 to M3. In the description below, the amounts of displacement of the respective cables from the predetermined reference position in the longitudinal axis direction of the shaft 102 are represented by $X_{C1a}$, $X_{C1b}$, $X_{C2a}$, and $X_{C2b}$.

The relationships between the displacement amounts $X_{C1a}$, $X_{C1b}$, $X_{C2a}$, and $X_{C2b}$ of the respective cables, and the turning angle $\theta_{pitch}$ of the pitch unit 401 about the first axis, the rotation angle $\theta_{roll}$ of the roll unit 402 about the second axis, and the open angle $\theta_{grip}$ of the jaws 405a and 405b are expressed as in the following Equations (2) to (5).

[Mathematical Formula 2]

$$X_{C_{1a}} = -R_{pitch} \cdot \theta_{pitch} + \frac{L}{\sin(\alpha_0)} - \frac{L}{\sin\left(\frac{1}{2}\theta_{grip} + \alpha_0\right)} \quad (2)$$

[Mathematical Formula 3]

$$X_{C_{1b}} = -R_{pitch} \cdot \theta_{pitch} - \frac{L}{\sin(\alpha_0)} + \frac{L}{\sin\left(\frac{1}{2}\theta_{grip} + \alpha_0\right)} \quad (3)$$

[Mathematical Formula 4]

$$X_{C_{2a}} = R_{pitch} \cdot \theta_{pitch} - R_{roll} \cdot \theta_{roll} \quad (4)$$

[Mathematical Formula 5]

$$X_{C_{2b}} = R_{pitch} \cdot \theta_{pitch} + R_{roll} \cdot \theta_{roll} \quad (5)$$

The second terms and the third terms of the right sides of Equations (2) and (3) shown above correspond to the amount of displacement of the rod 404 in the second axis direction shown above in Equation (1).

Further, the turning angle $\theta_{pitch}$ of the pitch unit 401 about the first axis, the open angle $\theta_{grip}$ of the jaws 405a and 405b, and the rotation angle $\theta_{roll}$ of the roll unit 402 about the second axis are expressed as in the following Equations (6) to (8), respectively.

[Mathematical Formula 6]

$$\theta_{pitch} = \frac{(X_{C_{2a}} + X_{C_{2b}}) - (X_{C_{1a}} + X_{C_{1b}})}{2} \quad (6)$$

[Mathematical Formula 7]

$$\theta_{grip} = 2\sin^{-1}\left(\frac{2L}{X_{C_{1b}} + X_{C_{1a}}}\right) - 2\alpha_0 \quad (7)$$

[Mathematical Formula 8]

$$\theta_{pitch} = \frac{X_{C_{2b}} - X_{C_{2a}}}{2} \quad (8)$$

Accordingly, by displacing the set of first forward and backward cables C1a and C1b and the set of second forward and backward cables C2a and C2b by a predetermined amount on the basis of the above Equations (6) to (8), it is possible to achieve a desired angle on each axis.

As can be seen from Equation (7), only the displacement amounts $X_{C1a}$ and $X_{C1b}$ of the set of first forward and backward cables C1a and C1b are involved in the open angle $\theta_{grip}$ of the jaws 405a and 405b. Likewise, as can be seen from Equation (8), only the displacement amounts $X_{C2a}$ and $X_{C2b}$ of the set of second forward and backward cables C2a and C2b are involved in the rotation angle $\theta_{roll}$ of the roll unit 402 about the second axis.

Further, as can be seen from Equation (6), the turning angle $\theta_{pitch}$ of the pitch unit 401 about the first axis is determined by the difference between the displacement amounts $X_{C1a}$ and $X_{C1b}$ of the set of first forward and backward cables C1a and C1b, and the displacement amounts $X_{C2a}$ and $X_{C2b}$ of the set of second forward and backward cables C2a and C2b.

D. Modifications of the Roll Unit

Figure 37:
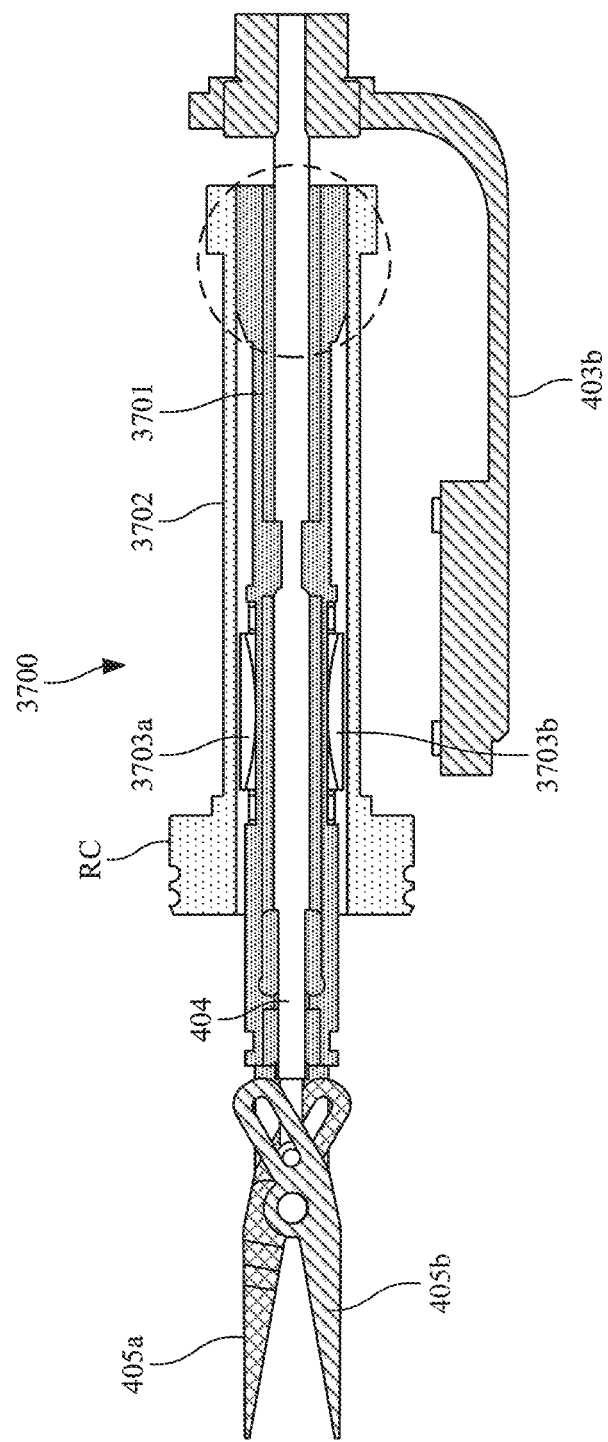
FIG. 37 is a diagram showing a cross-section of a roll unit 3700 according to a modification.

FIG. 37 shows a cross-section of a roll unit 3700 according to a modification. The roll unit 3700 shown in the drawing is divided into an inner surgical tool shaft portion 3701 and an outer surgical tool cover portion 3702 in the "roll unit 402" described above. The surgical tool shaft portion 3701 has a hollow cylindrical shape, and the rod 404 is inserted therein. Meanwhile, the surgical tool cover portion 3702 has a hollow cylindrical shape with an inner diameter equal to or larger than that of the surgical tool shaft portion 3701, and the surgical tool shaft portion 3701 is inserted therein. Further, the roll capstan RC is formed on the outer periphery of the surgical tool cover portion 3702, and the set of second forward and backward cables C2a and C2b (not shown in FIG. 37) is wound around the roll capstan RC. Also, in FIG. 37, the outer periphery of the surgical tool shaft portion 3701 and the inner wall surface of the surgical tool cover portion 3702 are joined at the portion surrounded by a dashed circle. Through this joining portion, the rotative force about the second axis is transmitted from the surgical tool cover portion 3702 to the surgical tool shaft portion 3701.

On the end side (the distal end side) of the joining portion surrounded by the dashed circle, the outer periphery of the surgical tool shaft portion 3701 and the inner wall surface of the surgical tool cover portion 3702 are slightly separated from each other, and there is a space in between. Using this space, strain detection elements 3703 are attached to several portions on the outer periphery of the surgical tool shaft portion 3701. Arithmetic processing is then performed on detection signals of the respective strain detection elements 3703, so that the external force applied to the jaws 405a and 405b at the end of the surgical tool can be calculated. Since the outer periphery of the surgical tool shaft portion 3701 and the inner wall surface of the surgical tool cover portion 3702 are not in contact with each other before reaching the joining portion surrounded by the dashed circle, any external force is not applied to the attachment positions of the strain detection elements 3703, except for the jaws 405a and 405b at the end of the surgical tool.

In the example shown in FIG. 37, a pair of strain detection elements 3703a and 3703b are attached to opposite sides in a direction ("Y direction", for example) orthogonal to the roll axis on the surface of the surgical tool shaft portion 3701. In such a case, arithmetic processing is performed on each detection signal of the pair of strain detection elements 3703a and 3703b, so that the amount of strain of the surgical tool shaft portion 3701 in the Y direction can be calculated. This amount of strain can be converted into the external force to be applied to the jaws 405a and 405b in the Y direction. Further, in a case where the external force to be applied to the jaws 405a and 405b in the X direction is to be calculated, a pair of strain detection elements (not shown in FIG. 37) are also attached to opposite sides in the X direction on the surface of the surgical tool shaft portion 3701, to perform the measurement. Note that strain generating structures may be formed at the positions of the respective strain detection elements 3703a and 3703b in the surgical tool shaft portion 3701.

Here, the strain detection elements 3703a and 3703b may be detection elements widely known in the art, such as capacitive sensors, semiconductor strain gauges, or a foil strain gauges, for example.

Alternatively, fiber Bragg grating (FBG) sensors manufactured with optical fibers may be used for the strain detection elements 3703a and 3703b. Here, an FBG sensor is a sensor formed by cutting a diffraction grating (a grating) along the long axis of an optical fiber, and is capable of detecting a change in the intervals between diffraction gratings due to expansion or contraction accompanying strain or temperature change caused by an acting force, and regarding the change in the intervals as a change in the wavelength of reflected light of incident light of a predetermined wavelength band (Bragg wavelength). The change in the wavelength detected from the FBG sensor can be then converted into strain, stress, or temperature change, which is the cause. An FBG sensor using an optical fiber has small transmission loss (or is not easily affected by noise from the outside), and thus, can maintain high detection accuracy under any conceivable environment. Further, an FBG sensor also has the advantage of being capable of coping with sterilization and high magnetic field environments that are necessary for medical treatment (see Patent Document 5, for example).

Figure 38:
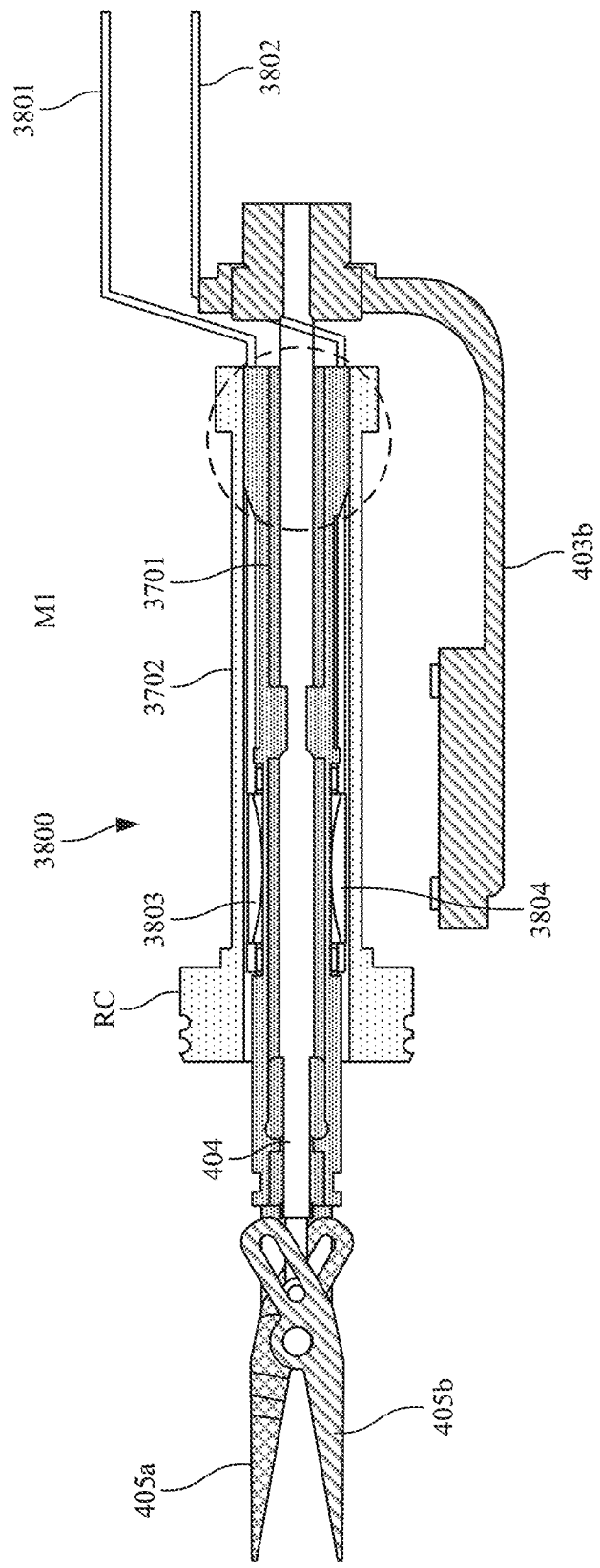
FIG. 38 is a diagram showing an example cross-sectional configuration of the roll unit 3700 using an FBG sensor.

FIG. 38 shows an example cross-sectional configuration of the roll unit 3700 in a case where FBG sensors are used for the strain detection elements. In the example shown in the drawing, two optical fibers 3801 and 3802 are inserted in the roll axis direction from the upper end surface of the roll unit 3700, using the space between the outer periphery of the surgical tool shaft portion 3701 and the inner wall surface of the surgical tool cover portion 3702. The two optical fibers 3801 and 3802 are then disposed on the opposite sides in the Y direction. Further, in the respective optical fibers 3801 and 3802, gratings are formed in the portions denoted by reference numerals 3803 and 3804, respectively, and can function as strain detection elements. Note that strain generating structures may be formed in the vicinities of the gratings 3803 and 3804 on the surgical tool shaft 3701.

E. Modifications of the Surgical Tool Unit

E-1. Modifications of the Method for Driving the Cables

It is most preferable to use electromagnetic rotary motors as the first to third motors M1 to M3. However, it is also possible to use some other types of actuators capable of rotating the drive capstans. Examples of other modifications of the actuators that pull the cables may include the following.

Piezoelectric linear-motion ultrasonic motors
Piezoelectric rotary ultrasonic motors
Hydraulic linear motors
Hydraulic rotary motors
Polymeric linear actuators
Electromagnetic linear motors
Shape-memory alloys Further, regardless of which kind of actuator is adopted, the actuators may be equipped with a speed reducer, a position detector, and an emergency brake mechanism. Here, examples of the speed reducers include gear reducers, wave gear reducers, planetary gear reducers, paradox planetary gear reducers, cable reducers, traction reducers, ball screws, sliding screws, and worm gears. Further, examples of the position detectors include magnetic encoders, optical encoders, and potentiometers.

E-2. Modifications of the Shape of the Jaws

In each drawing, the jaws are drawn in a relatively simple shape, for convenience sake. In practice, the shape of the jaws may be changed depending on the purpose of use of the surgical tool unit. For example, the following forms can be adopted.

Forceps
Bipolar forceps
Scissors
Staplers

E-3. Modifications of the Shaft

The shaft 102 is ideally a rigid member, but may be an elastic member such as a flexible endoscope. Further, in each drawing, the shaft 102 having a simple hollow cylindrical shape is shown for simplification. However, the shaft does not necessarily have a cylindrical shape. For example, a cross-section of the shaft 102 may have a polygonal shape or an elliptical shape, or its cross-sectional shape may change midway in the longitudinal axis direction.

E-4. Modifications of the Cables

A cable may be a bundle of metallic wires, a bundle of resin, or a mixture of a plurality of materials such as metal wires and resin. Also, a shaft 102 formed with a metal having a high rigidity may be used at a cable portion that is disposed inside the shaft 102 or the like and does not need to be curved, and be connected to a flexible cable that is used at a portion having a curve. In this manner, one cable may be formed. Examples of substitutes for the cables include the following.

Metallic or resin wires
Wires obtained by weaving thin metallic or resin wires having a small diameter

E-5. Modifications of the Idler Pulleys

In the examples described above, idler pulleys are used for adjusting the layout of the cables. With the use of idler pulleys, the sliding friction at a time when the cables are pulled can be reduced, and a smooth operation can be performed. In a case where sliding friction is to be reduced, idler pulleys each having a rotational bearing may be used.

However, the use of idler pulleys adds to the size of the mechanism, and the number of components becomes larger. Therefore, to further reduce the size of the surgical tool unit end portion 101, cables may be laid out along guide grooves formed in the mechanism without any idler pulley.

F. Example Applications of the Surgical Tool Unit

F-1. Example Application to a Surgical Robot (a Computer-Aided Surgery System)

Figure 39:
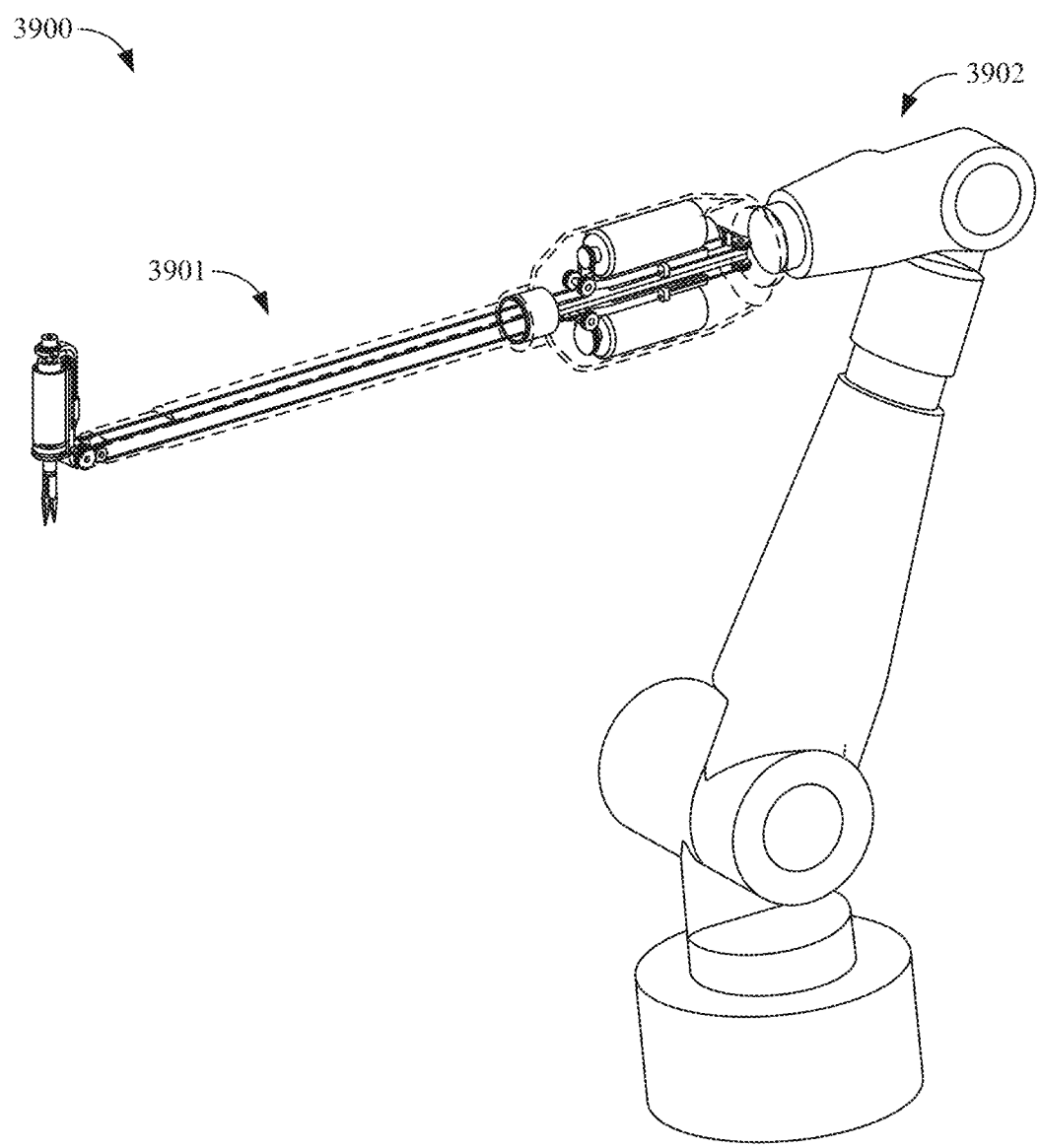
FIG. 39 is a diagram showing an example external configuration of a surgical robot 3900 using a surgical tool unit.

FIG. 39 shows an example external configuration of a surgical robot 3900 using a surgical tool unit according to this embodiment. The surgical robot 3900 shown in the drawing includes an arm 3901 having a multi-link structure, and a surgical tool unit 3902 is attached to the end of the arm 3901. The surgical tool unit 3902 may be replaceable. The surgical robot 3900 is used in laparoscopic surgery, for example, and the surgical tool unit end portion 101 is inserted into an abdominal cavity through a trocar (not shown), to perform an operation such as gripping and cutting of an affected part.

The surgical robot 3900 shown in the drawing is used as the slave device in a master-slave system, for example, and the arm 3901 and the surgical tool unit 3902 are driven in accordance with an instruction from the master device (not shown). Further, a bilateral control method is applied to this type of master-slave system, for example.

Note that the arm 3901 may be a robot of any mechanism type such as a polar-coordinate robot, a cylindrical coordinate robot, a Cartesian coordinate robot, a vertical articulated robot, a horizontal articulated robot, a parallel link robot, or a remote center of motion (RCM) robot, for example.

Further, in a case where the surgery support system 3900 is a surgical robot that supports laparoscopic surgery, the arm 3901 is preferably a vertical articulated arm or a remote center of motion (RCM) arm that has its remote rotation center at a position away from the driving rotation center and performs a pivoting (fixed-point) motion, so as to achieve compactness of the mechanism, ease of a pivoting motion generation at the site of a trocar, and the like.

Furthermore, although FIG. 39 shows an example configuration of a surgical robot to which only one surgical tool unit can be attached, the present technology can also be applied to a surgical robot of a type to which a plurality of surgical tool units can be simultaneously attached to perform laparoscopic surgery.

F-2. Applicability to an Operating Unit

Figure 40:
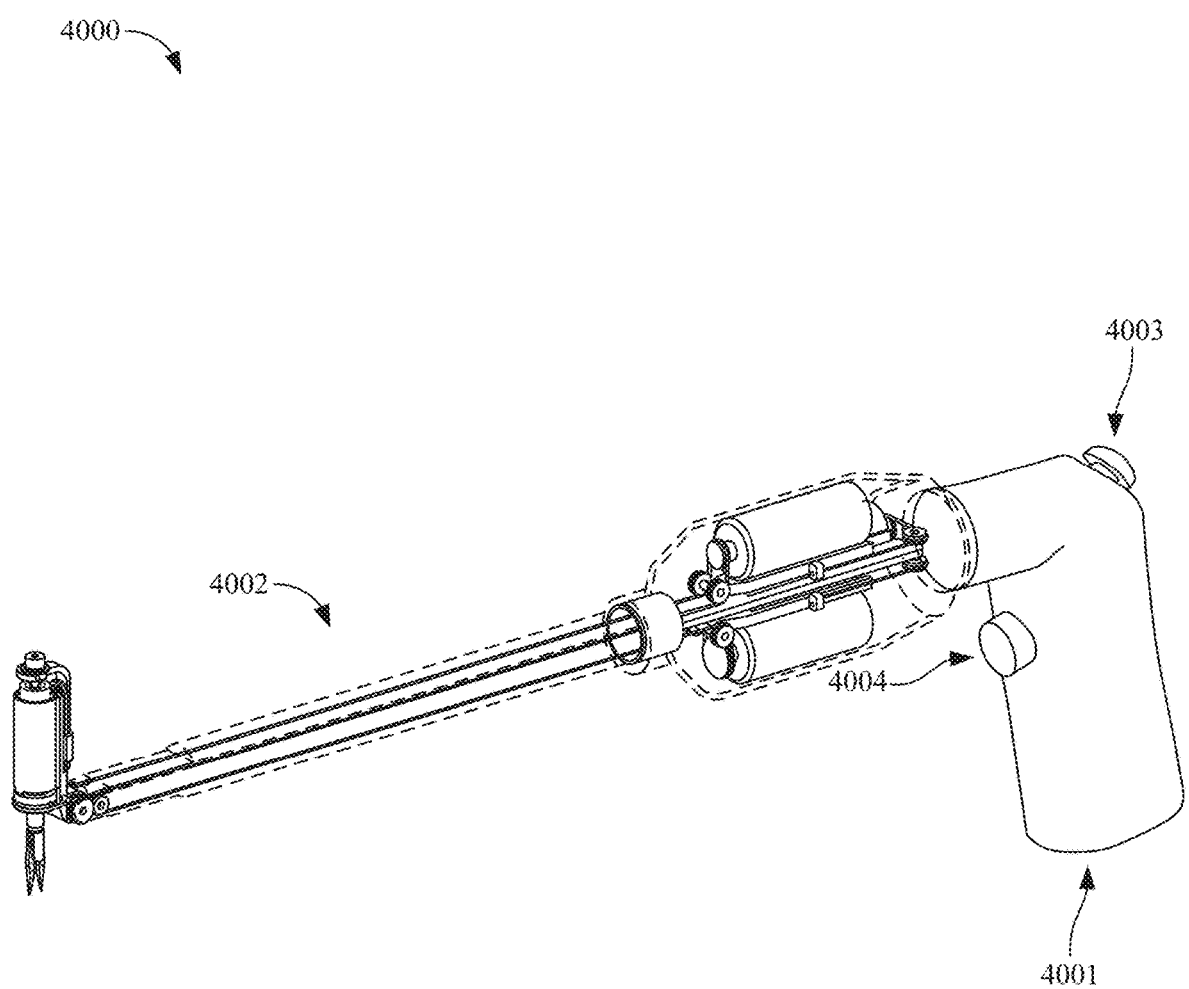
FIG. 40 is a diagram showing an example external configuration of an operating unit 4000.

FIG. 40 shows an example external configuration of an operating unit 4000 using a surgical tool unit according to this embodiment. The operating unit 4000 includes a handle unit 4001 that is directly held and operated by a user by hand, and a surgical tool unit 4002 is attached to the end of the handle unit 4001. The surgical tool unit 4002 may be replaceable.

The handle unit 4001 may include a joystick 4003 that can be handled with a thumb to designate a desired orientation of the posture of the surgical tool unit end portion of the surgical tool unit 4002. The handle unit 4001 may also include a button 4004 that can be pushed with an index finger to issue an instruction for an opening and closing operation of the jaws.

A controller (not shown) may be installed in the handle unit 4001. This controller calculates the turning angle $\theta_{pitch}$ of the pitch unit 401 about the first axis, the rotation angle $\theta_{roll}$ of the roll unit 402 about the second axis, and the open angle $\theta_{grip}$ of the jaws 405a and 405b, in accordance with the amount of operation of the joystick 4003 or the button 4004. These angles are converted into the amounts of rotation of the respective motors, and a control signal is output to the surgical tool unit drive unit 103.

G. Effects

In the surgical tool unit 100 according to the present disclosure, rotation about the second axis parallel to the roll axis of the roll unit 402 is the degree of freedom of the distal end (but the degree of freedom in gripping of the jaws is excluded). Thus, a wider range of movement can be achieved. Specifically, the pitch unit 401 has a rotational degree of freedom to turn approximately ±80 degrees about the first axis parallel to the pitch axis, and the roll unit 402 has a rotational degree of freedom of approximately ±150 degrees about the second axis.

Further, in the surgical tool unit 200 according to the present disclosure, the open angle $\theta_{grip}$ of the pair of jaws 405a and 405b is determined by the difference in displacement in the longitudinal axis direction of the shaft 102 between the first forward cable C1a and the first backward cable C1b (see the above Equation (7), for example). Also, the rotation angle $\theta_{roll}$ of the roll unit 402 about the second axis is determined by the difference in displacement in the longitudinal axis direction of the shaft 102 between the second forward cable C2a and the second backward cable C2b (see the above Equation (8), for example). Further, the turning angle $\theta_{pitch}$ of the pitch unit 401 about the first axis is determined by the difference in the average value of displacement in the longitudinal axis direction of the shaft 102 between the set of first forward and backward cables C1a and C1b and the set of second forward and backward cables C2a and C2b (see the above Equation (6), for example).

In short, the control model for the surgical tool unit 100 according to the present disclosure is simple. Accordingly, when the surgical tool unit 100 is used in a surgical robot (see FIG. 39), control is easy. When the surgical tool unit 100 is used in an operating unit (see FIG. 40), the operation is easy for the operator.

Further, the surgical tool unit 100 according to the present disclosure is equipped with strain detection elements (see FIGS. 37 and 38) provided on the roll unit 402, and thus, can detect the external force applied to the jaws at the end. In this case, the distance from the first axis to the jaw at the end can also be short.

INDUSTRIAL APPLICABILITY

The technology according to the present disclosure has been described in detail so far, with reference to specific embodiments. However, it is obvious that those skilled in the art can make modifications to and substitutions of the embodiments without departing from the scope of the technology according to the present disclosure.

In this specification, embodiments in which the technology according to the present disclosure is applied to a surgical tool to be used in a surgical robot have been mainly described. However, the subject matter of the technology according to the present disclosure is not limited to these embodiments. The technology according to the present disclosure can be applied to robots in various fields other than medical care, such as precision work robots. The technology according to the present disclosure can also be applied to a grip-type operating unit and a precision work device a user can operate while gripping it with a hand.

In short, the technology according to the present disclosure has been described through examples, and the descriptions in this specification should not be interpreted in a restrictive manner. The claims should be taken into account in understanding the subject matter of the technology according to the present disclosure.

Note that the technology according to the present disclosure may also be embodied in the configurations described below.

(1) A surgical tool including:
a shaft;
a pitch unit that is connected to an end of the shaft and is able to turn about a first axis;
a roll unit that is supported and is rotatable about a second axis with respect to the pitch unit; and
a grip unit that is supported and is linearly movable in the second axis direction with respect to the roll unit.

(2) The surgical tool according to (1), in which the second axis is located at a position offset from the first axis.

(3) The surgical tool according to any one of (1) and (2), further including a pair of jaws that are attached to a lower end of the roll unit in the second axis direction, and open and close in conjunction with linear motion of the grip unit in the second axis direction.

(4) The surgical tool according to (3), in which
the grip unit supports a rod through which the roll unit is inserted in the second axis direction, and
the pair of jaws are supported by an open-close shaft near the lower end of the roll unit, and include a cam that converts linear motion of the rod in the second axis direction into motion in an opening and closing direction.

(5) The surgical tool according to (4), further including:
a set of first forward and backward cables that pulls the grip unit in the second axis direction; and
a set of second forward and backward cables that pulls the roll unit about the second axis.

(6) The surgical tool according to (5), in which
the set of first forward and backward cables has a portion secured to the grip unit, and is laid out to be folded back in the second axis direction via a grip pulley provided on the roll unit.

(7) The surgical tool according to (5) or (6), in which
the set of second forward and backward cables is wound around a roll capstan provided on the roll unit.

(8) The surgical tool according to (7), in which
a forward cable and a backward cable of the set of second forward and backward cables are wound around the roll capstan, to overlap each other by 180 degrees about the second axis from opposite directions, and not to be in contact with each other while being separated in a height direction of the second axis.

(9) The surgical tool according to any one of (5) to (8), further including:
a first idler pulley unit that switches the set of first forward and backward cables to a longitudinal axis direction of the shaft; and
a second idler pulley unit that switches the set of second forward and backward cables to the longitudinal axis direction of the shaft.

(10) The surgical tool according to (9), in which
the first idler pulley unit includes a first idler pulley that rotates about the first axis, and a first adjacent idler pulley that is adjacent to the first idler pulley and has a rotation axis parallel to the first axis, and
the second idler pulley unit includes a second idler pulley that rotates about the first axis, and a second adjacent idler pulley that is adjacent to the second idler pulley and has a rotation axis parallel to the first axis.

(11) The surgical tool according to (10), in which
the set of second forward and backward cables is wound around the second idler pulley from an opposite direction to a direction in which the set of first forward and backward cables is wound around the first idler pulley.

(12) The surgical tool according to (11), further including:
a first actuator that rotates a first drive capstan and pulls the set of first forward and backward cables in a longitudinal axis direction of the shaft; and
a second actuator that rotates a second drive capstan and pulls the set of second forward and backward cables in the longitudinal axis direction of the shaft.

(13) The surgical tool according to (12), further including:
a first slide base that secures the first actuator and the first drive capstan, and slides in the longitudinal axis direction of the shaft;
a second slide base that secures the second actuator and the second drive capstan, and slides in the longitudinal axis direction of the shaft;

a third actuator that rotates a third drive capstan; and
a set of third forward and backward cables that is wound around the third drive capstan, ends of the third forward and backward cables being secured to the first slide base and the second slide base, respectively, in which
forward and backward motion of the first slide base and the second slide base is caused by rotation of the third drive capstan.

(14) A surgery support system including a surgical tool, and an arm to which the surgical tool is attached,
the surgical tool including:
a shaft;
a pitch unit that is connected to an end of the shaft and is able to turn about a first axis;
a roll unit that is supported and is rotatable about a second axis with respect to the pitch unit; and
a grip unit that is supported and is linearly movable in the second axis direction with respect to the roll unit.

(15) A surgical operating unit including a surgical tool, and a handle unit to which the surgical tool is attached, the surgical tool including:
a shaft;
a pitch unit that is connected to an end of the shaft and is able to turn about a first axis;
a roll unit that is supported and is rotatable about a second axis with respect to the pitch unit; and
a grip unit that is supported and is linearly movable in the second axis direction with respect to the roll unit.

REFERENCE SIGNS LIST

100 Surgical tool unit
101 Surgical tool unit end portion
102 Shaft
103 Surgical tool unit drive unit
3900 Surgical robot
3901 Arm
3902 Surgical tool unit
4000 Operating unit
4001 Handle unit
4002 Surgical tool unit
4003 Joystick
4004 Button

The invention claimed is:
1. A surgical tool, comprising:
a shaft;
a hollow cylinder connected to an end of the shaft, wherein
the hollow cylinder is rotatable about a first axis, and the first axis is parallel to a pitch axis with respect to the shaft;
a through hole in the hollow cylinder;
a rod inserted into the through hole, wherein
the rod is supported by the hollow cylinder, and
the rod is rotatable about a second axis with respect to the hollow cylinder;
an open-close shaft at a lower end of the rod;
a pair of first jaws supported by each of the rod and the hollow cylinder, wherein the pair of first jaws is linearly movable in a second axis direction with respect to the hollow cylinder;
a pair of second jaws attached to the lower end of the rod in the second axis direction, wherein
the pair of second jaws is configured to open and close in the second axis direction, the open and close of the pair of second jaws is in conjunction with a linear motion of the pair of first jaws, the pair of second jaws is supported by the open-close shaft, and the pair of second jaws includes a cam, wherein the cam is configured to convert a linear motion of the rod in the second axis direction into a motion in an opening and a closing direction of the pair of second jaws;

a set of first forward and backward cables configured to pull the pair of first jaws in the second axis direction; and a set of second forward and backward cables configured to pull the rod about the second axis.

2. The surgical tool according to claim 1, wherein the second axis is located at a position offset from the first axis.

3. The surgical tool according to claim 1, further comprising a grip pulley, wherein the set of first forward and backward cables has a portion secured to the the pair of first jaws, and the set of first forward and backward cables is folded back in the second axis direction via the grip pulley.

4. The surgical tool according to claim 1, further comprising a roll capstan, wherein the set of second forward and backward cables is wound around the roll capstan.

5. The surgical tool according to claim 4, wherein a forward cable of the set of second forward and backward cables is wound around the roll capstan about the second axis in a first direction, a backward cable of the set of second forward and backward cables is wound around the roll capstan about the second axis in a second direction opposite to the first direction, the forward cable overlaps the backward cable by 180 degrees about the second axis, and the forward cable is not in contact with the backward cable in a height direction of the second axis.

6. The surgical tool according to claim 1, further comprising:

a first idler pulley unitconfigured to switch the set of first forward and backward cables to a longitudinal axis direction of the shaft; and a second idler pulley unit configured to switch the set of second forward and backward cables to the longitudinal axis direction of the shaft.

7. The surgical tool according to claim 6, wherein the first idler pulley unit includes:

a first idler pulley configured to rotate about the first axis; and a first adjacent idler pulley adjacent to the first idler pulley, wherein a rotation axis of the first adjacent idler pulley is parallel to the first axis, and the second idler pulley unit includes:

a second idler pulley configured to rotate about the first axis; and a second adjacent idler pulley adjacent to the second idler pulley, wherein a rotation axis of the second adjacent idler pulley is parallel to the first axis.

8. The surgical tool according to claim 7, wherein the set of second forward and backward cables is wound around the second idler pulley from a first direction to a second direction, the first direction is opposite to the second direction, and the set of first forward and backward cables is wound around the first idler pulley in the second direction.

9. The surgical tool according to claim 8, further comprising:

a first drive capstan;

a second drive capstan;

a third drive capstan;

a first actuator configured to:

rotate the first drive capstan; and pull the set of first forward and backward cables in the longitudinal axis direction of the shaft; and a second actuator configured to:

rotate the second drive capstan; and pull the set of second forward and backward cables in the longitudinal axis direction of the shaft.

10. The surgical tool according to claim 9, further comprising:

a first slide base configured to:

secure the first actuator and the first drive capstan; and slide in the longitudinal axis direction of the shaft;

a second slide base configured to:

secure the second actuator and the second drive capstan; and slide in the longitudinal axis direction of the shaft;

a third actuator configured to rotate the third drive capstan; and a set of third forward and backward cables wound around the third drive capstan, wherein ends of the set of third forward and backward cables are configured to be secured to the first slide base and the second slide base, respectively, and each of forward motion of the first slide base and backward motion of the second slide base is based on the rotation of the third drive capstan.

11. A surgery support system, comprising:

a surgical tool; and an arm to which the surgical tool is attached, wherein the surgical tool includes a shaft;

a hollow cylinder connected to an end of the shaft, wherein the hollow cylinder is rotatable about a first axis, and the first axis is parallel to a pitch axis with respect to the shaft;

a through hole in the hollow cylinder;

a rod inserted into the through hole, wherein the rod is supported by the hollow cylinder, and the rod is rotatable about a second axis with respect to the hollow cylinder;

an open-close shaft at a lower end of the rod;

a pair of first jaws supported by each of the rod and the hollow cylinder, wherein the pair of first jaws is linearly movable in a second axis direction with respect to the hollow cylinder;

a pair of second jaws attached to the lower end of the rod in the second axis direction, wherein the pair of second jaws is configured to open and close in the second axis direction, the open and close of the pair of second jaws is in conjunction with a linear motion of the pair of first jaws, the pair of second jaws is supported by the open-close shaft, and the pair of second jaws includes a cam, wherein the cam is configured to convert a linear motion of the rod in the second axis direction into a motion in an opening and a closing direction of the pair of second jaws;

a set of first forward and backward cables configured to pull the pair of first jaws in the second axis direction; and a set of second forward and backward cables configured to pull the rod about the second axis.

12. A surgical operating unit, comprising:

a surgical tool; and a handle unit to which the surgical tool is attached, wherein the surgical tool includes:

a shaft;

a hollow cylinder connected to an end of the shaft, wherein
  the hollow cylinder is rotatable about a first axis, and
  the first axis is parallel to a pitch axis with respect to the shaft;

a through hole in the hollow cylinder;

a rod inserted into the through hole, wherein
  the rod is supported by the hollow cylinder, and
  the rod is rotatable about a second axis with respect to the hollow cylinder;

an open-close shaft at a lower end of the rod;

a pair of first jaws supported by each of the rod and the hollow cylinder, wherein the pair of first jaws is linearly movable in a second axis direction with respect to the hollow cylinder;

a pair of second jaws attached to the lower end of the rod in the second axis direction, wherein
  the pair of second jaws is configured to open and close in the second axis direction,
  the open and close of the pair of second jaws is in conjunction with a linear motion of the pair of first jaws,
  the pair of second jaws is supported by the open-close shaft, and
  the pair of second jaws includes a cam, wherein the cam is configured to convert a linear motion of the rod in the second axis direction into a motion in an opening and a closing direction of the pair of second jaws;

a set of first forward and backward cables configured to pull the pair of first jaws in the second axis direction; and a set of second forward and backward cables configured to pull the rod about the second axis.

* * * * *